US009533073B1

(12) United States Patent
Kong et al.

(10) Patent No.: US 9,533,073 B1
(45) Date of Patent: Jan. 3, 2017

(54) MICROVASCULAR STAMP FOR PATTERNING OF FUNCTIONAL NEOVESSELS

(71) Applicant: The Board of Trustees of the University of Illinois, Urbana, IL (US)

(72) Inventors: Hyunjoon Kong, Champaign, IL (US); Rashid Bashir, Champaign, IL (US); Jaehyun Jeong, Champaign, IL (US); Vincent Chan, Urbana, IL (US); Chaenyung Cha, Penndel, PA (US); Pinar Zorlutuna, Cambridge, MA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/709,726

(22) Filed: May 12, 2015

Related U.S. Application Data

(63) Continuation of application No. 13/788,023, filed on Mar. 7, 2013, now Pat. No. 9,050,180.

(60) Provisional application No. 61/650,073, filed on May 22, 2012.

(51) Int. Cl.
| | |
|---|---|
| *C12N 5/071* | (2010.01) |
| *A61L 27/52* | (2006.01) |
| *A61L 27/50* | (2006.01) |
| *A61L 27/54* | (2006.01) |
| *A61L 27/26* | (2006.01) |
| *A61L 27/38* | (2006.01) |
| *C12N 5/00* | (2006.01) |
| *C12N 5/02* | (2006.01) |

(52) U.S. Cl.
CPC .............. *A61L 27/507* (2013.01); *A61L 27/26* (2013.01); *A61L 27/3834* (2013.01); *A61L 27/52* (2013.01); *A61L 27/54* (2013.01); *A61L 2300/64* (2013.01); *A61L 2430/00* (2013.01)

(58) Field of Classification Search
None
See application file for complete search history.

(56) References Cited

U.S. PATENT DOCUMENTS

| 4,791,061 A | 12/1988 | Sumino et al. |
| 6,621,685 B1 | 9/2003 | Cho et al. |

OTHER PUBLICATIONS

Dhariwala et al., "Rapid prototyping of tissue-engineering constructs, using photopolymerizable hydrogels and stereolithography", Tissue Eng., 2004 (Abstract Only).
Nishi et al., "Basic fibroblast growth factor impregnated hydrogel microspheres for embolization of cerebral arteriovenous malformations", ASAIO J., 1998 (Abstract Only).
Fournier et al., "Biological molecule-impregnated polyester: an in vivo angiogenesis study", Biomaterials, 1996 (Abstract Only).
Van Tomme et al., "In situ gelling hydrogels for pharmaceutical and biomedical applications", International Journal of Pharmaceuticals, 355:1-18 (2008).
Jeong et al., "In Situ Cell Encapsulation into a Vascularized Hydrogel Matrix using a Stereolithography (SLA)" AIChE Annual Meeting, Nashville, TN, 2009 (Oral Presentation).
Jeong et al., "Design of Cell-Encapsulating Hydrogel for Neovascularization: Intergration of Material Chemistry and Microfabrication", Oct. 2010 (Oral Presentation).
Chen et al., "Spatio-temporal VEGF and PDGR Delivery Patterns Blood Vessel Formation and Maturation", Pharmaceutical Research, 24(2):258-264 (2007).
Silva et al., "Effects of VEGF temporal and spatial presentation on angiogenesis", Biomaterials, 31:1235-1241 (2010).
Khademhosseini et al., "Microscale technologies for tissue engineering and biology", PNAS 103(8):2480-2487 (2006).
Dike et al., "Geometric Control of Switching Between Growth, Apoptosis, and Differentiation During Angiogenesis Using Micropatterned Substrates", In Vitro Cell. Dev. Biol. 35:441-448 (1999).
Tsuda et al., "Cellular control of tissue architectures using a three-dimensional tissue fabrication technique" Biomaterials, 28:4939-4946 (2007).
Campbell et al., "Engineered spatial patterns of FGF-2 immobilized on fibrin direct cell organization", Biomaterials, 26:6762-6770 (2005).
Gbureck et al., "Direct Printing of Bioceramic Implants with Spatially Localized Angiogenic Factors", Adv. Mater. 19:795-800 (2007).
Du et al., "Rapid generation of spatially and temporally controllable long-range concentration gradients in a microfluidic device", Lap Chip, 9:761-767 (2009).
Barkefors et al., "A fluidic device to study directional angiogenesis in complex tissue and organ culture models", Lab Chip, 9:529-535 (2009).
Cha et al., "Decoupled control of stiffness and permeability with a cell-encapsulating poly (ethylene glycol) dimethacrylate hydrogel" Biomaterials, 31:4864-4871 (2010).
Arcaute et al., "Stereolithography of Three-Dimensional Bioactive Poly(Ethylene Glycol) Constructs with Encapsulated Cells", Annals of Biomedical Engineering, 34(9):1429-1441 (2006).
Chan et al., "Three-dimensional photopatterning of hydrogels using stereolithography for long-term cell encapsulation", Lab Chip, 10:2062-2070 (2010).
Cha et al., "Biodegradable Polymer Crosslinker: Independent Control of Stiffness, Toughness, and Hydrogel Degradation Rate", Adv. Funct. Matter. 19:3056-3062 (2009).
DeVolder et al., "Three dimensionally flocculated proangiogenic microgels for neovascularization", Biomaterials, 31:6494-6501 (2010).
Schmidt et al., "Hydrogels used for cell-based drug delivery", Journal of Biomedical Materials Research Part A, pp. 1113-1122 (2008).

(Continued)

*Primary Examiner* — Nancy J Leith
(74) *Attorney, Agent, or Firm* — McDonnell Boehnen Hulbert & Berghoff LLP

(57) ABSTRACT

The invention provides compositions and methods for making and using microvascular stamps for stimulation and spatial organization of neovessels in tissue.

12 Claims, 25 Drawing Sheets

(56) References Cited

OTHER PUBLICATIONS

Tabata et al., "Biodegradation of Hydrogel Carrier Incorporating Fibroblast Growth Factor", Tissue Engineering, 5 (2):127-138 (1999).
Nichol et al., "Cell-laden microengineered gelatin methacrylate hydrogels", Biomaterials, 3(21):5536-5544 (2010).
Jeong et al., "'Living' Microvascular Stamp for Patterning of Functional Neovessels; Orchestrated Control of Matrix Property and Geometry", Advanced Materials, 24:58-63 (2012).
Du et al., "Sequential assembly of cell-laden hydrogel constructs to engineer vascular-like microchannels", Biotechnol. Bioeng., 108(7):1693-1703 (2011).
Moon et al., "Biomimetic hydrogels with pro-angiogenic properties", Biomaterials, 31(14):3840-3847 (2010).
Mayer & Heckel, "Biologically Active Molecules with a "Light Switch"", Angewendte Chemie, 45:4900-4921 (2006).
Nemir et al., "PEGDA Hydrogels with Patterned Elasticity: Novel Tools for the Study of Cell Response to Substrate Rigidity", Biotechnology and Bioengineering, 105:636 (2009).
Lin et al., "Hydrogels in controlled release formulations: Network design and mathematical modeling", Advanced Drug Delivery Reviews, 58:1379-1408 (2006).

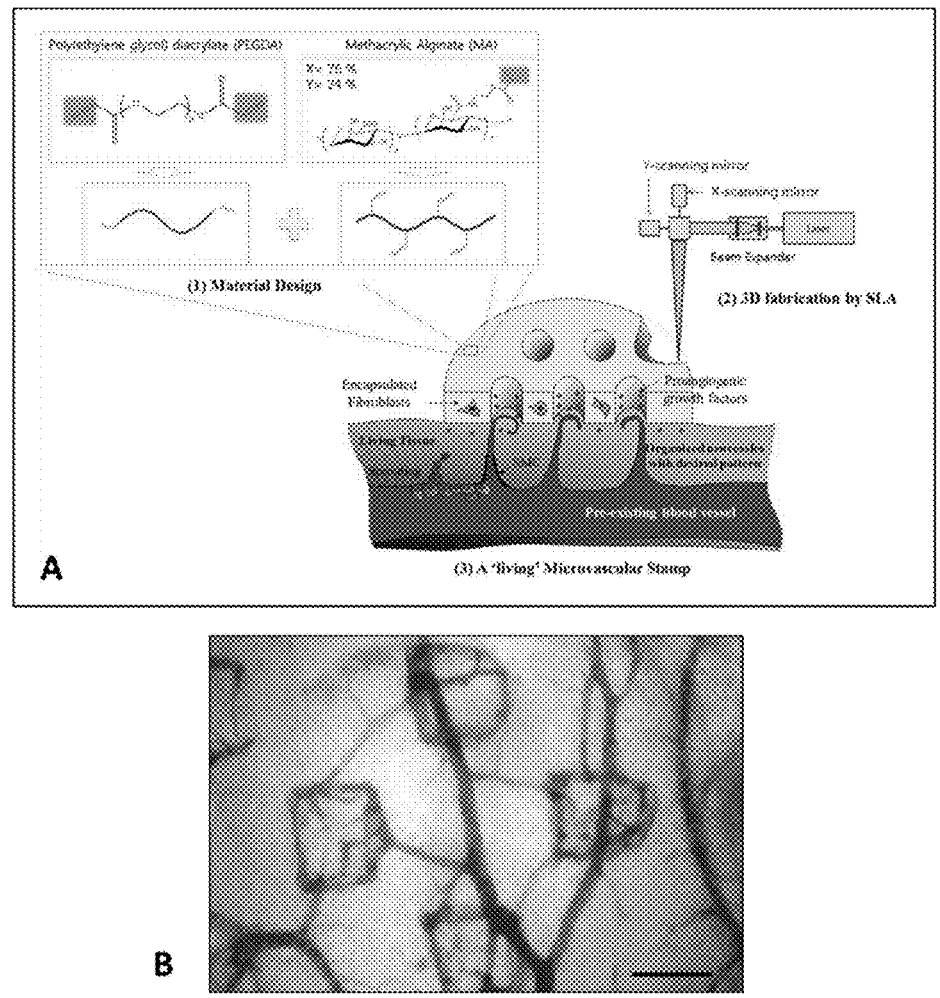
Figure 1A-B

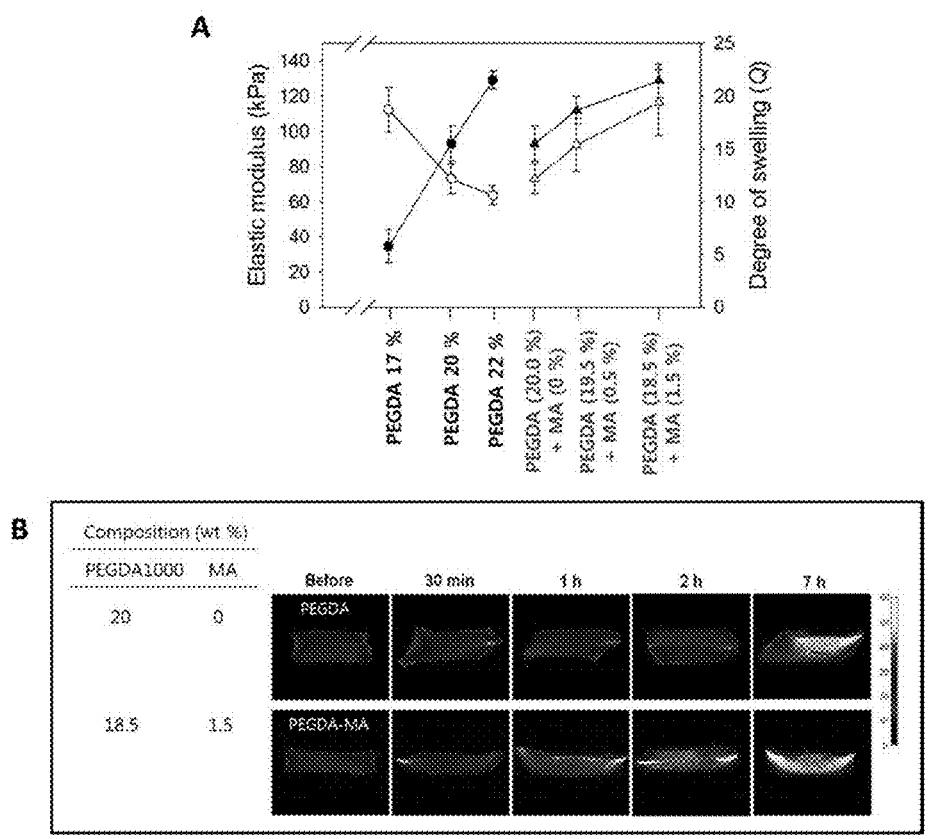
Figure 2A-B

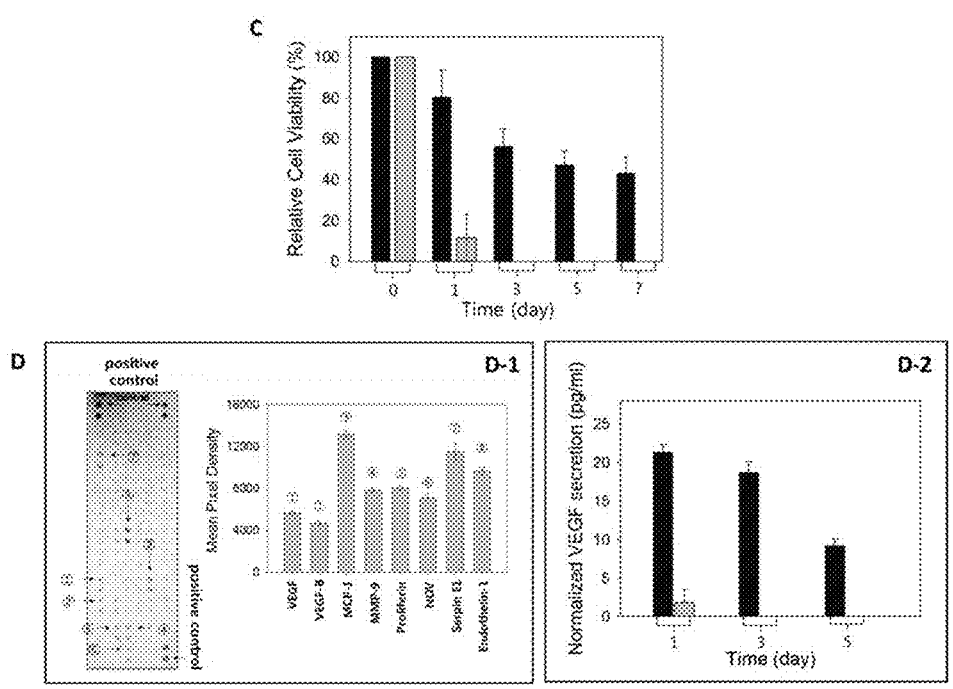
Figure 2C-D

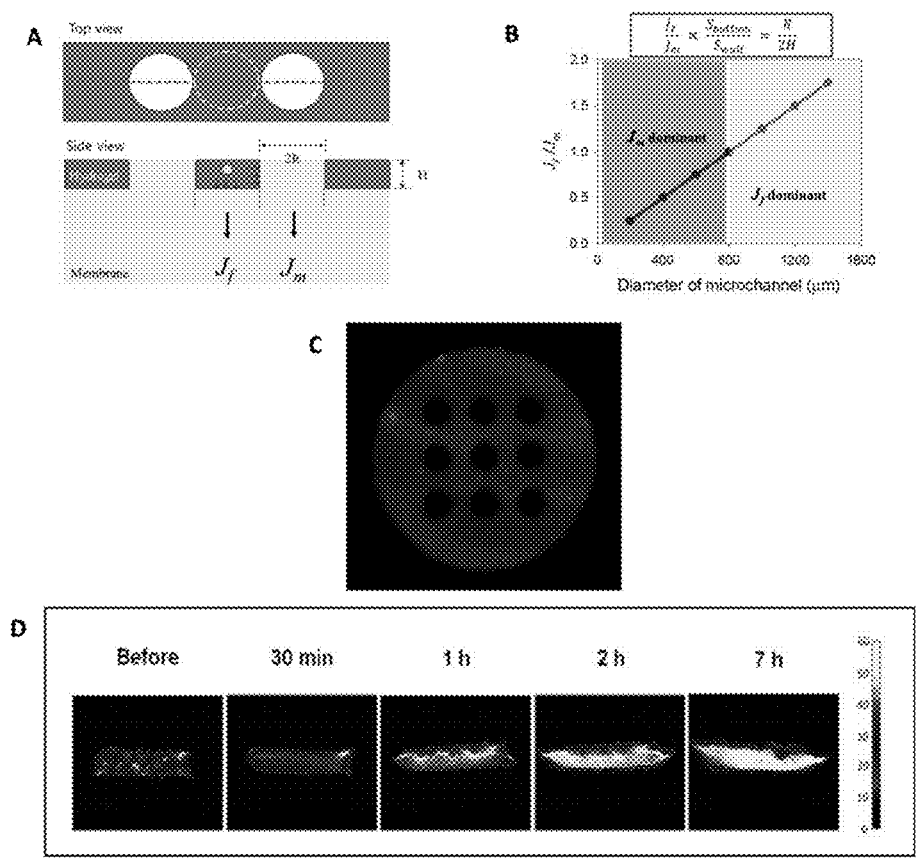
Figure 3A-D

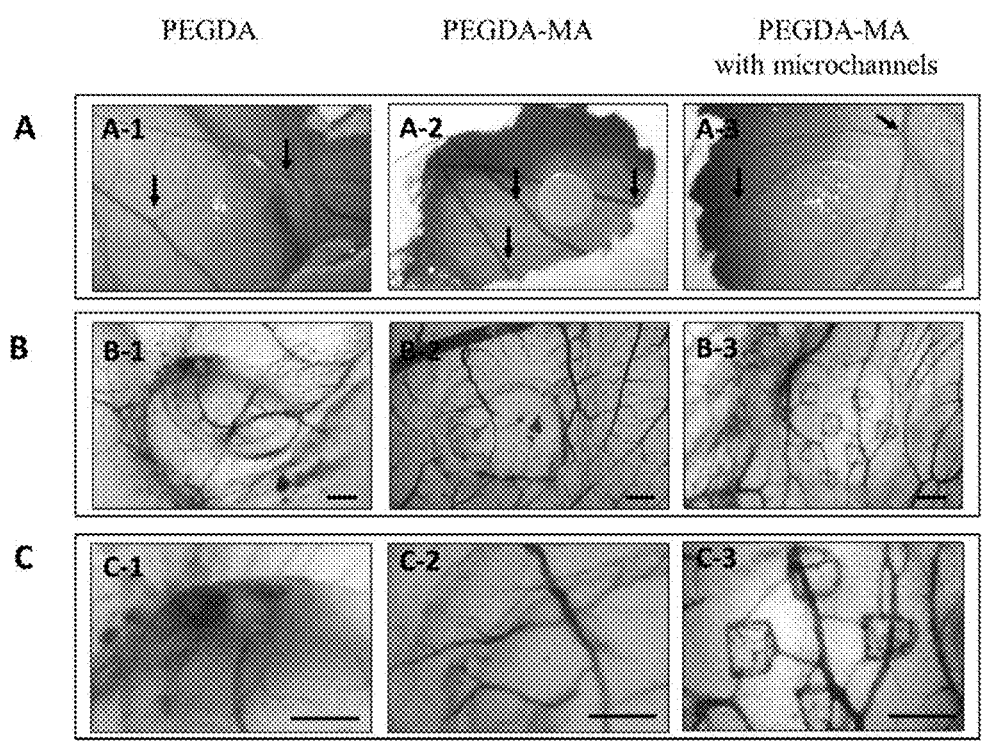
Figure 4A-C

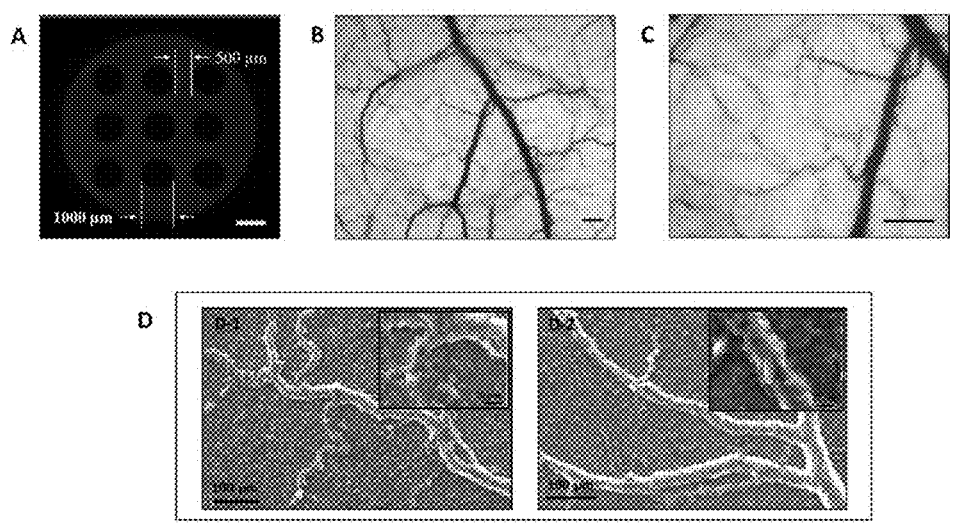
Figure 5A-D

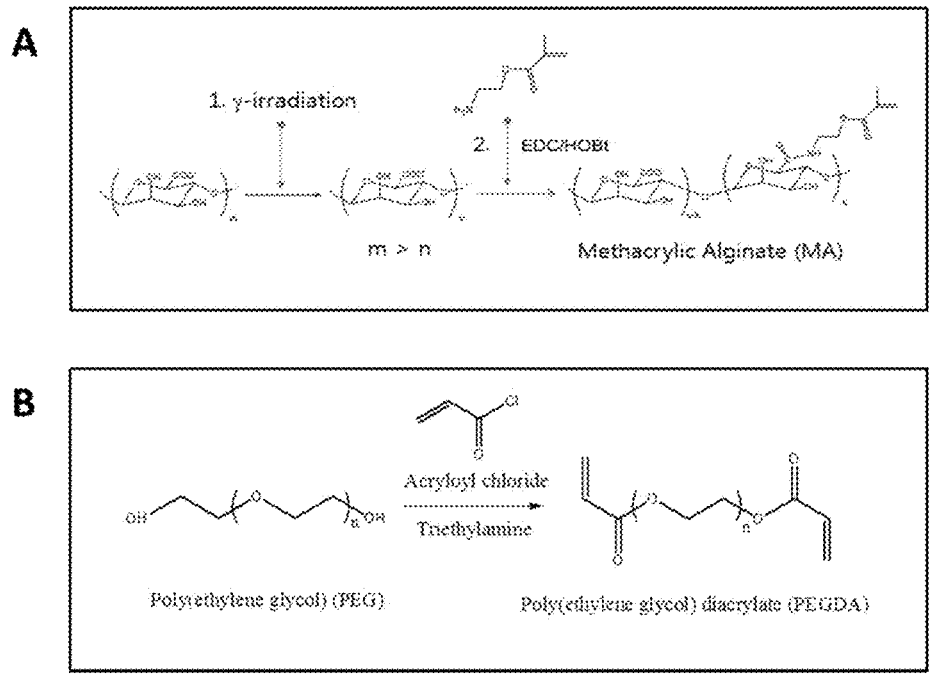
Figure 6A-B

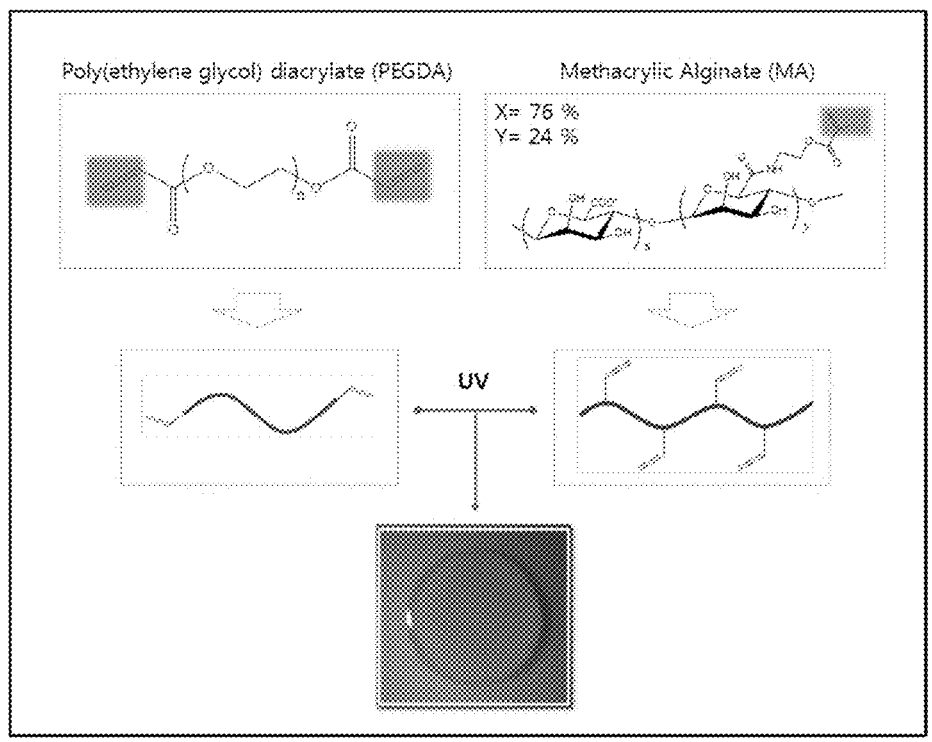
Figure 7 Hydrogel formulation scheme.

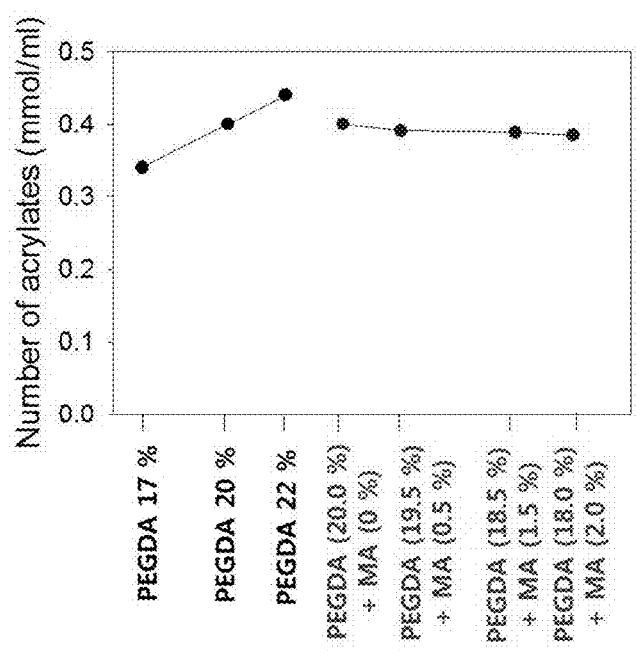
Figure 8 Calculation of total acrylic groups of the hydrogels.

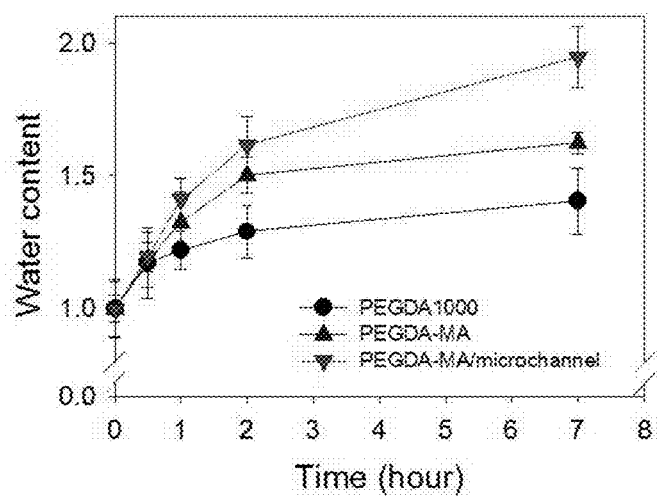
Figure 9 Quantitative analysis of water diffusion into the hydrogel.

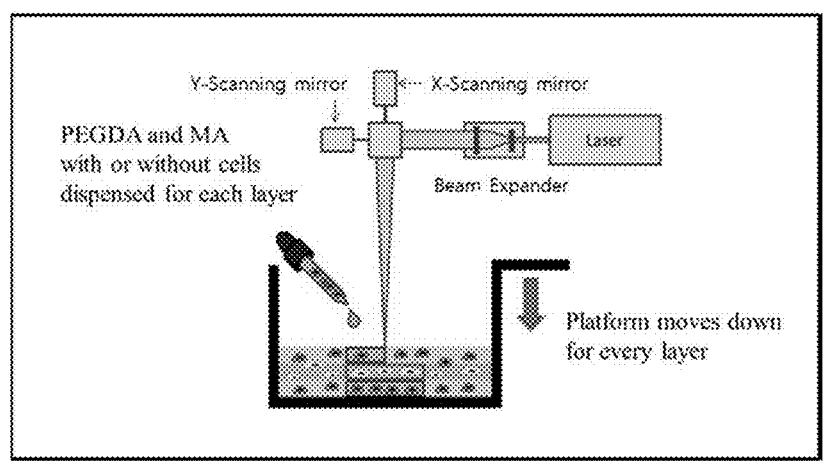
Figure 10 Bottom-up Process for cell-encapsulated hydrogel assembly.

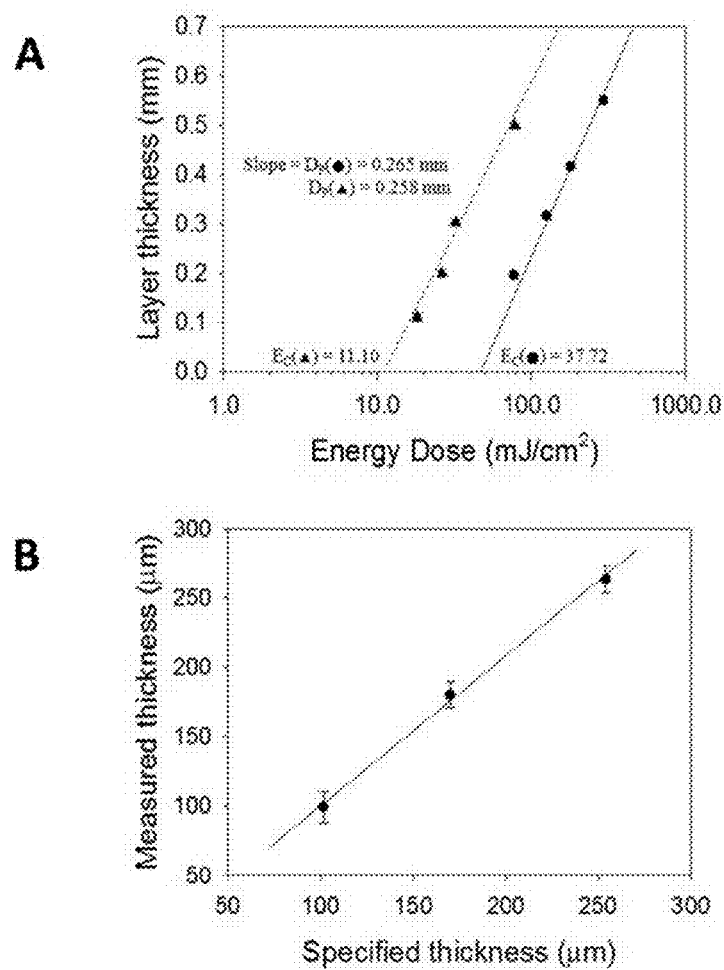
Figure 11 A-B Computer-Aided Design (CAD)-based Hydrogel assembly.

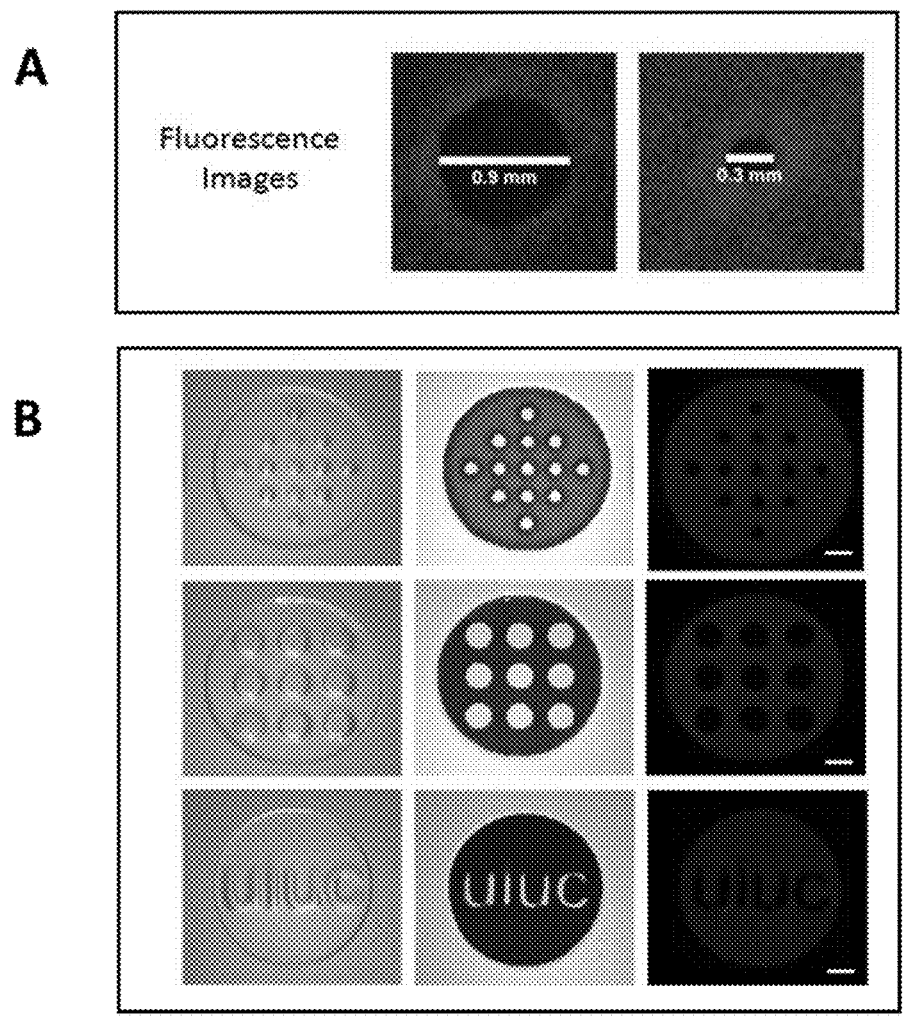
Figure 12A-B

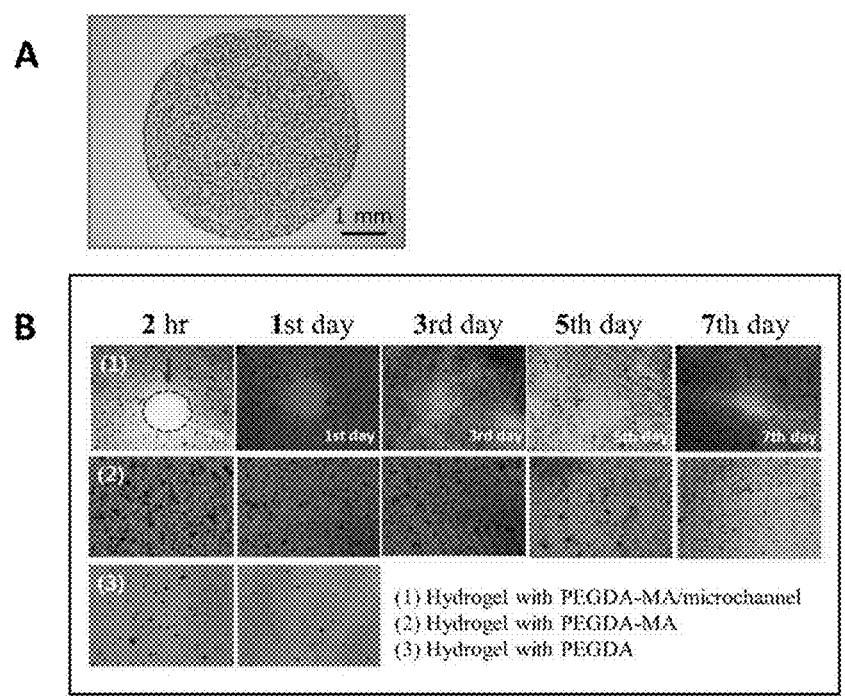
Figure 13A-B NIH/3T3 cells cultured for seven days while being encapsulated within hydrogels.

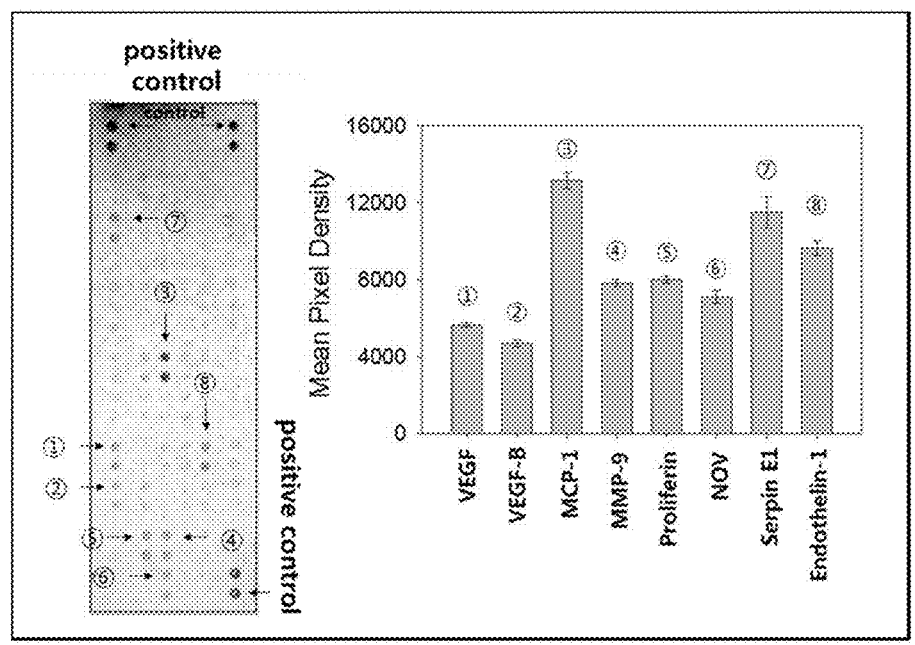
Figure 15 Proangiogenic growth factor excretion.

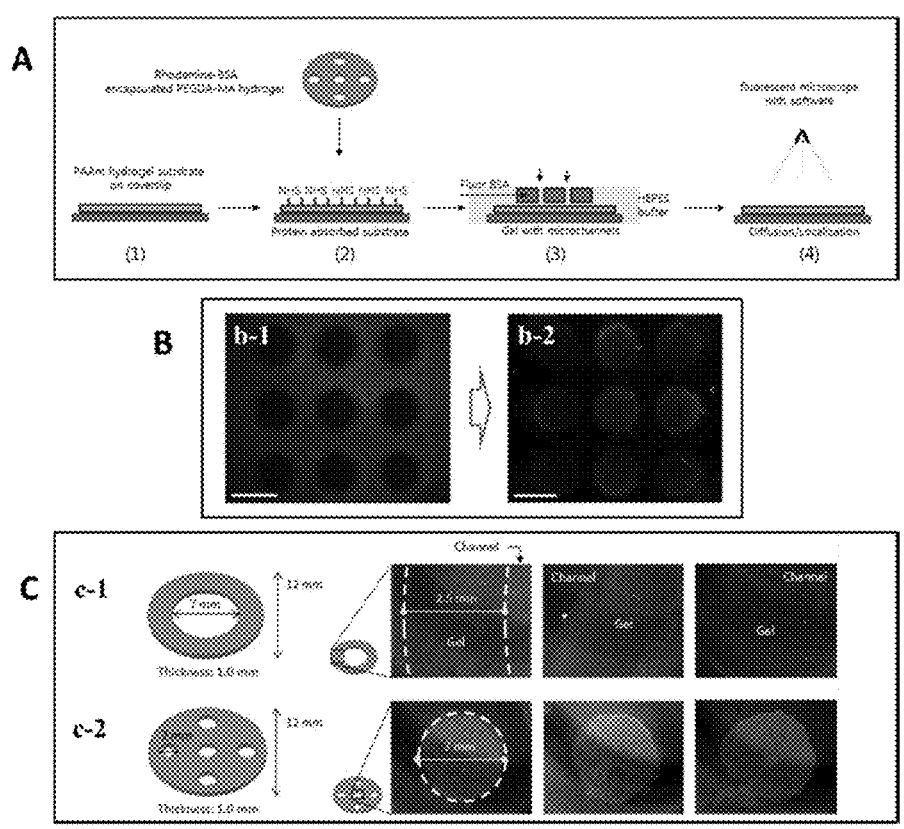
Figure 16A-C

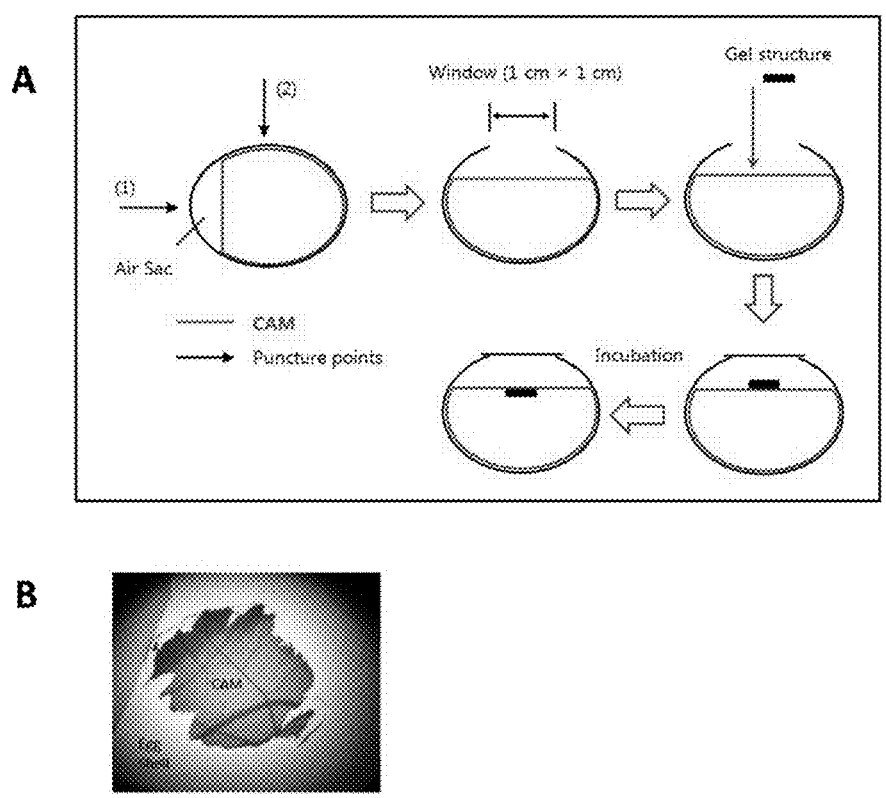
Figure 17A-B

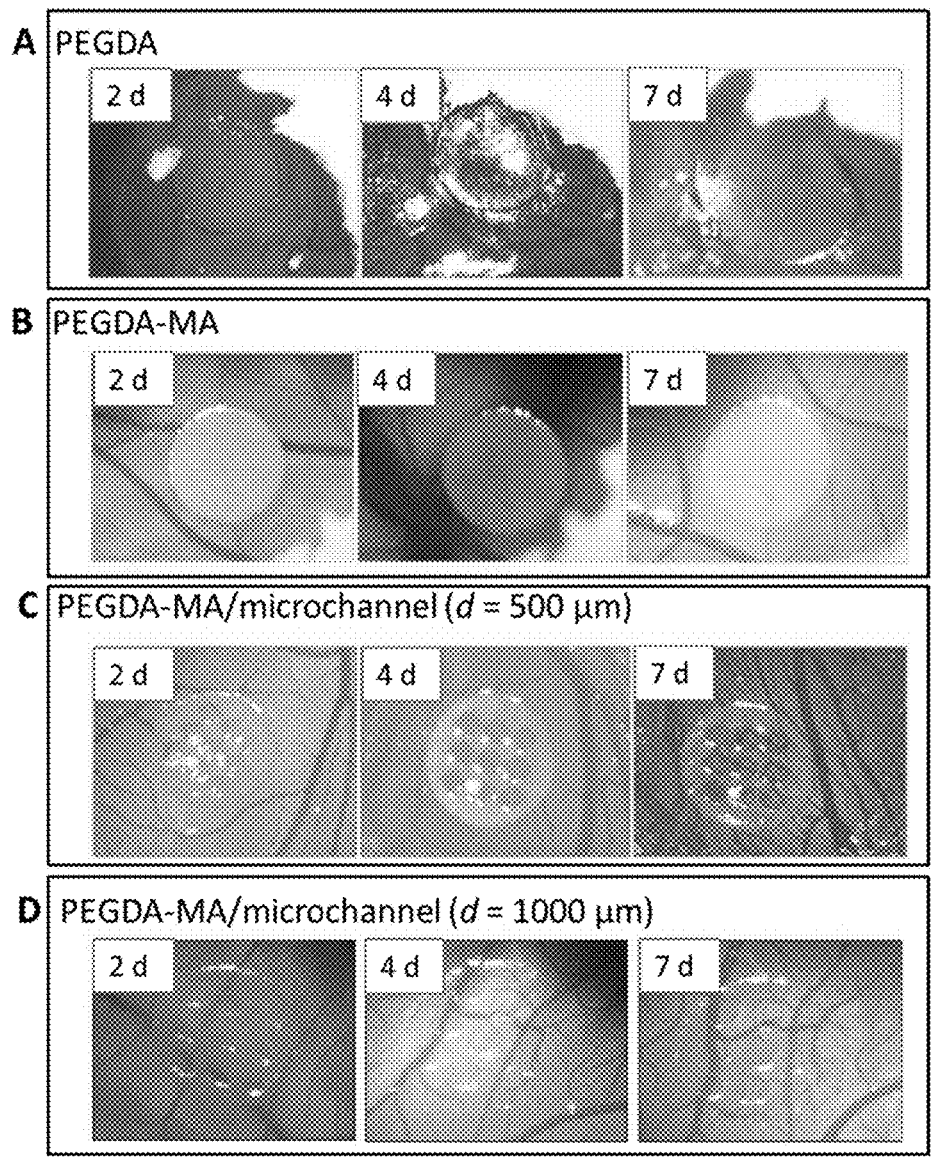
Figure 18A-D

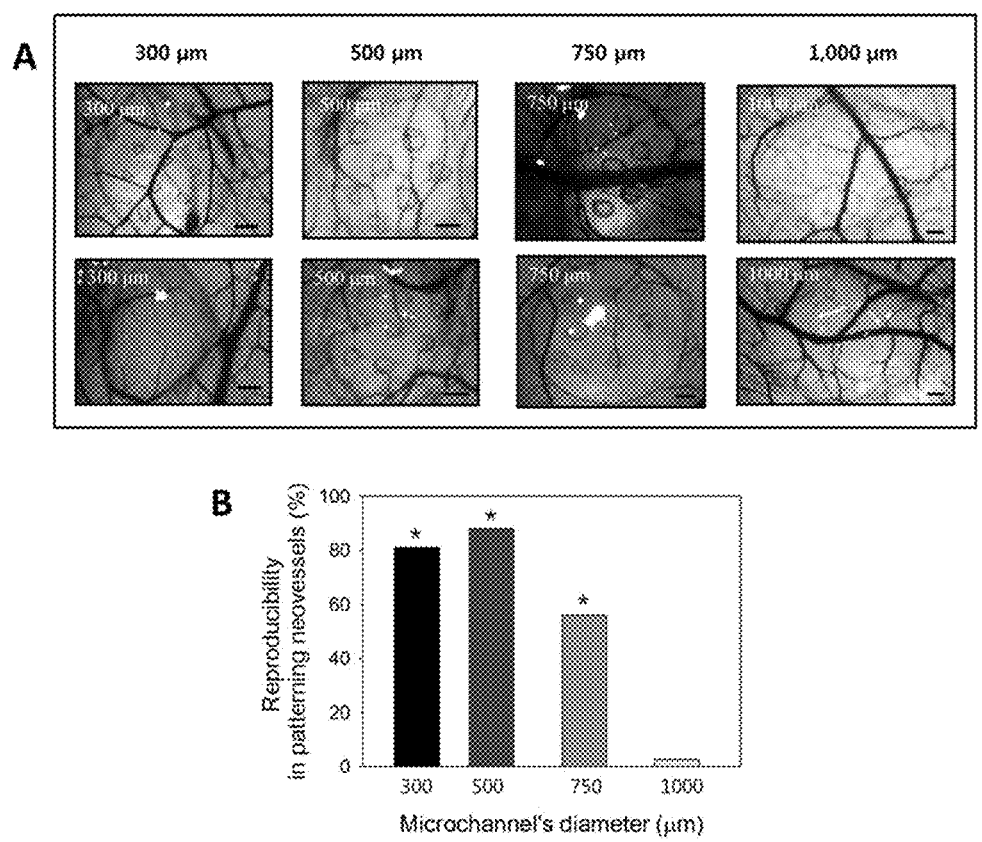
Figure 19A-B

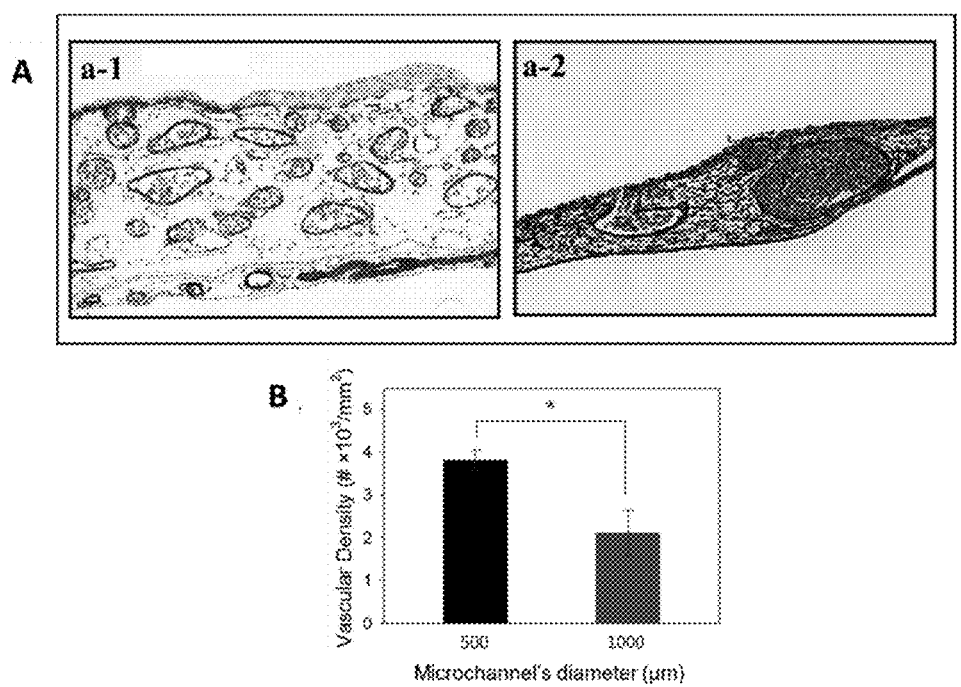
Figure 20A-B

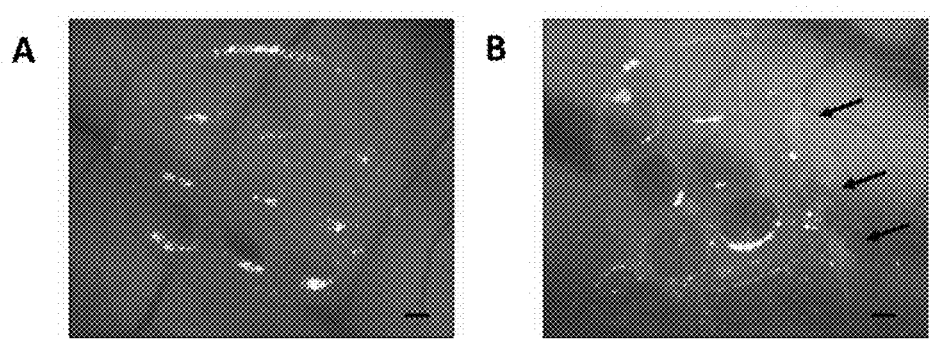
Figure 21A-B

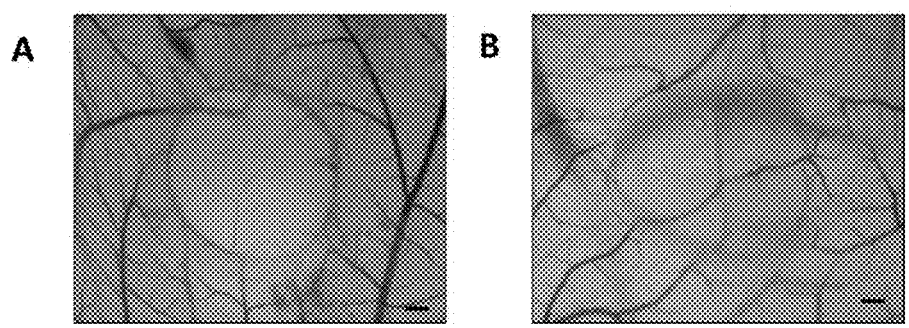
Figure 22A-B

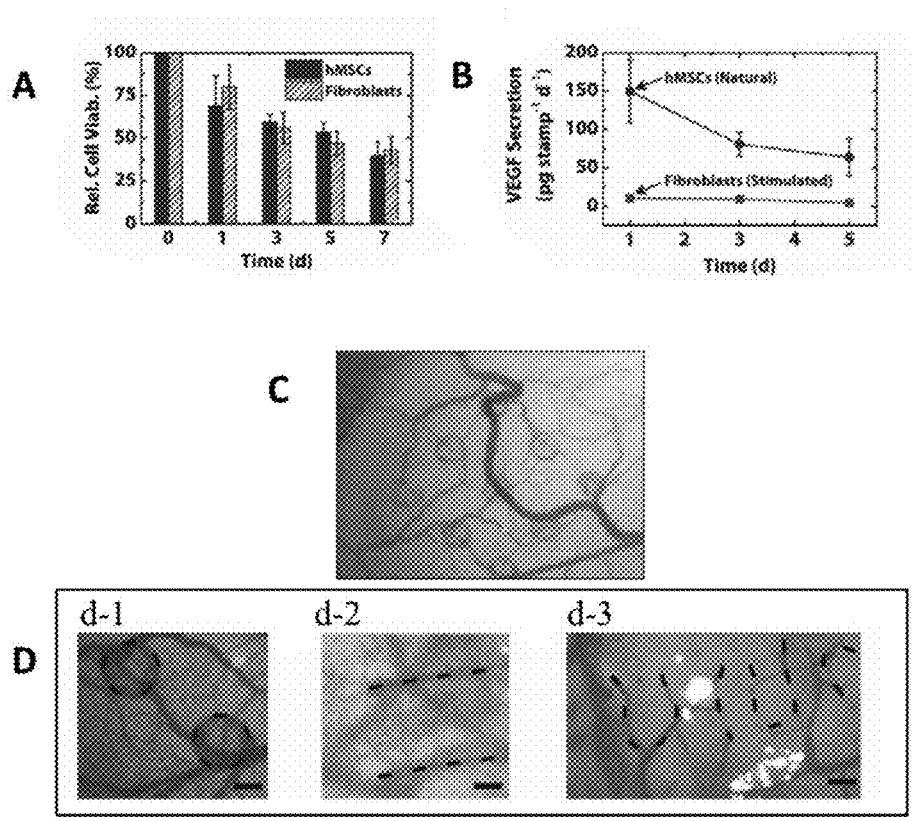
Figure 23A-D

MICROVASCULAR STAMP FOR PATTERNING OF FUNCTIONAL NEOVESSELS

PRIORITY

This application is a continuation of U.S. Ser. No. 13/788,023, filed on Mar. 7, 2013, which claims the benefit of U.S. Provisional application 61/650,073, filed May 22, 2012. These applications are incorporated herein by reference in their entirety.

GOVERNMENT INTERESTS

This work was supported by US Army Telemedicine & Advanced Technology Research Center (TATRC) (W81XWH-08-1-0701), and National Science Foundation (CAREER: DMR-0847253, STC-EBICS Grant CBET-0939511, IGERT DGE-0965918). The United States government has certain rights in this invention.

BACKGROUND OF THE INVENTION

Neovessels play a critical role in homeostasis, regeneration, and pathogenesis of tissues and organs[1-2], and their spatial organization is a major factor to influence the vascular function[3]. It has been proposed that an ability to control growth direction and spacing of neovessels over physiologically relevant lengths ranging from about 100 µm to about 500 µm can provide a better understanding and controllability of neovessel formation[3-7]. However, a technology to accomplish this challenging goal is still lacking.

Prior studies have demonstrated that spatiotemporal distribution of multiple proangiogenic growth factors in a 3D tissue can control growth direction of neovessels and also their macroscale spacing[7-8]. In these studies, various polymeric scaffolds were assembled by welding a growth factor-releasing layer with a growth factor-free layer, while varying layer thickness at the millimeter scale. To further control spatial organization of the neovessels at a length scale required to uniformly perfuse 3D tissue, various micropatterning, ink-jet printing and microfluidic techniques were used to control spatiotemporal distribution of proangiogenic factors or direct the adhesion pattern of endothelial cells at micrometer scales[9-15]. However, there have been no reports of regulating the microscale spacing between functional neovessels, through which blood flows in vivo, using microfabrication techniques. Spacing of neovessels is important for proper vascularization of tissue.

SUMMARY OF THE INVENTION

One embodiment of the invention provides microvascular stamp comprising one or more types of cells encapsulated in a poly(ethylene glycol) (PEGDA) and methacrylic polymer cross-linked hydrogel, wherein the cross-linked hydrogel comprises microchannels. The one or more types of cells can secrete one or more proangiogenic factors, growth factors, or antiangiogenic factors or combinations thereof. The microchannels can be about 100 µm to about 2.5 mm in diameter and the on-center spacing between the microchannels can be about 100 µm to about 2.5 mm. The ratio between the flux of growth factors through the microchannel wall of the stamp ($J_m$) can be larger than the flux through the bottom of the stamp with the same cross-sectional area as the microchannel ($J_f$). The stamp can be about 100 µm to about 5 mm thick. The stamp can have an elastic modulus of about 10 kPa to about 140 kPa. The stamp can be populated with neovessels. The one or more types of cells express one or more fusion proteins comprising a growth factor, proangiogenic factor, or antiangiogenic factor fused to a protein light switch.

Another embodiment of the invention provides a method of making a microvascular stamp. The method comprises encapsulating cells in a poly(ethylene glycol) (PEGDA) and methacrylic polymer hydrogel; crosslinking the hydrogel with a stereolithographic apparatus to form a cross-linked hydrogel; and incorporating microchannels into the cross-linked hydrogel with a stereolithographic apparatus. The microvascular stamp can be contacted with a tissue in vivo or in vitro.

Still another embodiment of the invention is a method of inducing growth of new blood vessels in a tissue. The method comprises contacting one or more of the microvascular stamps with the tissue, wherein the microvascular stamp induces the growth of new blood vessels in the tissue. The one or more types of cells can express one or more fusion proteins comprising a growth factor, proangiogenic factor, or antiangiogenic factor fused to a protein light switch. The one or more microvascular stamps can be illuminated with light at a wavelength of about 450 nm to about 500 nm. The microscale spacing between functional new blood vessels can be regulated by the microchannel diameter and spacing. The microscale spacing between the new blood vessels can be about 100 µm to about 2.5 mm on-center.

Yet another embodiment of the invention provides a method of treating a tissue defect in a subject in need thereof. The method comprises administering one or more microvascular stamps to the subject, thereby treating the tissue defect. The one or more types of cells can express one or more fusion proteins comprising a growth factor, proangiogenic factor, or antiangiogenic factor fused to a protein light switch. The one or more microvascular stamps can be illuminated with light at a wavelength of about 450 nm to about 500 nm. The microvascular stamp can be administered to the subject by injection, implantation, endoscopic delivery, or by catheter.

Another embodiment of the invention provides a kit comprising a microvascular stamp, wherein the stamp is immersed in a medium that retains viability of the cells.

Therefore, the invention provides microvascular stamps that remain stable at the implant or graft site and that support expression of proangiogenic factors such that controlled microspacing of functional neovessels is directed. The live cells of the microvascular stamp provide an unexpected advancement in patterning neovessels for proper vascularization because of their intrinsic properties of synthesizing and secreting multiple angiogenic factors in a sustained manner.

BRIEF DESCRIPTION OF THE DRAWINGS

FIG. 1A shows a schematic diagram of stereolithographic assembly of a 'living' microvascular stamp. The stamp was built by engineering rigidity and permeability of a hydrogel of poly(ethylene glycol) diacrylate (PEGDA) and methacrylic alginate (MA), encapsulating cells that secrete multiple proangiogenic factors into the hydrogel, and further incorporating microchannels with a geometry appropriate to release the cell-secreted proangiogenic factors through the microchannel lumen. The encapsulation of cells and spatial organization of microchannels within the stamp was implemented via in situ cross-linking reaction of the polymers mixed with cells using a 3-D stereolithographic (SLA) fabrication technique. FIG. 1B shows that implantation of the stamp on the living tissue developed a pattern of neovessels equivalent to the pattern of microchannel engraved into the microvascular stamp.

FIG. 2 a-d shows characterization of stiffness and permeability of the PEGDA and PEGDA-MA hydrogels. a. Increasing polymer concentration of the pure PEGDA hydrogel resulted in the increase of elastic modulus (●) and the decrease of degree of swelling (○). In contrast, increasing mass fraction of MA in the PEGDA-MA hydrogel while keeping total polymer concentration constant at 20% led to increases of both the elastic modulus (▲) and the degree of swelling (Δ). b. Water protons visualized with magnetic resonance imaging (MRI) were diffused into PEGDA-MA hydrogel more rapidly than the pure PEGDA hydrogel. Pseudo-color of MRI images represents the intensity of water proton (see the scale bar on the right). c. During seven days of cell culture, the NIH/3T3 cells encapsulated in the PEGDA-MA hydrogel (▨) (left bar) remained more viable than those encapsulated in the PEGDA hydrogel (▨) (right bar). The relative cell viability was quantified by normalizing the absorbance value of samples treated with MTT reagent to that measured at Day 0. d. Proangiogenic growth factors including VEGF, VEGF-B, MCP-1, MMP-9, proliferin, NOV, Serpin E1 and Endothelin-1 were secreted from NIH/3T3 fibroblasts encapsulated within a PEGDA-MA hydrogel, (d-1). The amount of VEGF secreted by cells for five days was found to be larger with cells encapsulated within the PEGDA-MA hydrogel (▨) (left bar) as compared with those encapsulated within the PEGDA hydrogel (▨) (right bar) (d-2).

FIG. 4 a-c shows the fibroblast-encapsulated hydrogels implanted onto chick embryo chorioallantoic membrane (CAM). a. Images shown were captured right after the cell-hydrogel constructs were implanted. Arrows in (a) represent blood vessels that existed before implantation of the cell-hydrogel construct. b. Images displayed represent top views of the CAM exposed to the cell-hydrogel construct for seven days. The cell-hydrogel constructs were removed right before imaging the CAM. The implantation of PEGDA-MA hydrogel with microchannels (diameter=500 μm) uniquely resulted in neovessels grown along the circular pattern of microchannel in the hydrogel (b-3). In addition, the spacing between the circular neovessel was the same as that between microchannels in the cell-hydrogel construct. No defined neovessel pattern was found with implantations of the microchannel-free PEGDA hydrogel and the microchannel-free PEGDA-MA hydrogel (b-1 & b-2). The implant sites were further magnified in (c) (scale bars represent 500 μm).

FIG. 5 a-d shows validation of diffusion-based model by incorporating microchannels inappropriate to derive the neovessel pattern. a. The microchannel diameter of the PEGDA-MA hydrogel was increased to 1,000 μm while keeping the spacing of microchannels constant at 500 μm. b. As predicted by modeling in FIG. 2, the implantation of the cell-hydrogel construct on CAM did not result in any defined pattern of neovessels. Instead, neovessels grew in a tortuous pattern. The implant site was further magnified in (c) (scale bar represents 500 μm). d. In addition, the wall of blood vessel imaged with SEM (d-1) was less compact as compared with the neovessel developed by implanting the hydrogel containing microchannels with a diameter of 500 μm (d-2).

FIG. 6 a-b shows synthesis of gel-forming methacrylic alginate (MA) and poly (ethylene glycol) diacrylates (PEGDA).

FIG. 7 shows a hydrogel formulation scheme.

FIG. 8 shows the calculation of total acrylic groups of the hydrogels. Total number of acrylates in each hydrogel was varied with PEGDA concentration. In contrast, increasing mass fraction of MA while keeping total polymer concentration constant at 20% led to minimally change the total number of acrylates in each hydrogel.

FIG. 9 shows a quantitative analysis of water diffusion into the hydrogel. Increase of water amount within a hydrogel was quantified by dissecting the MRI images in FIGS. 1c and 2d and counting the number of pixels colored by red and yellow colors, which represents the water protons bound to a gel matrix. The water amount quantified at different time points was normalized to the initial water amount. Increase of water content within the PEGDA-MA hydrogel (▲) was faster than that within the PEGDA hydrogel (•). Incorporation of microchannels into the PEGDA-MA hydrogel (▼) further accelerated the increase of water count.

FIG. 10 shows the bottoms-up process for cell-encapsulated hydrogel assembly.

FIG. 11 a-b shows the computer-aided design (CAD)-based hydrogel assembly. 3D CAD model was generated using AutoCAD 2009 (Autodesk) and exported to stereolithography format. The SLA software, 3D lightyear v1.4 (3D Systems) was used to slice the 3D models into a series of 2D layers from a user-specified thickness. a. The penetration depth ($D_p$) and critical exposure energy ($E_c$) parameters, which are specific to a desired pre-gelled solution, were acquired from energy dose characterizations and entered into the SLA software. The dependency of the layer thickness on the irradiation dose became larger as the molecular weight of PEGDA was increased from 1000 (•) to 3400 (▲) b. The thickness of hydrogel layer could be predicted by the calibration curve in (a).

FIG. 12 a-b shows hydrogels assembled to present varied forms of microchannels. a. The diameter of microchannel introduced with SLA was decreased down to 300 μm. b. Example of the hydrogel disk with varied diameters, spacing and shape of microchannels.

FIG. 13 a-b shows NIH/3T3 cells cultured for seven days while being encapsulated within hydrogels.

FIG. 15 shows proangiogenic growth factors including VEGF, VEGF-B, MCP-1, MMP-9, proliferin, NOV, and Serpin E1, which were secreted from NIH/3T3 fibroblasts adhered to a 2D poly(styrene) substrate.

FIG. 16 a-c shows an analysis of the role of microchannel geometry of a protein-releasing hydrogel in protein localization around the pattern of microchannels. a. Schematic of the experimental set-up to examine localization of proteins diffused from the hydrogel with microchannels. (1) The microscopic platform was prepared on a cover glass. Following the treatment with 0.1 M sodium hydroxide, the coverslip was siliconized with 3-aminopropyltriethoxy silane (APES; Sigma) followed by modification with 0.5% glutaraldehyde (Sigma) in PBS. The 1.0 mL of pre-gel solution was prepared with 200 μL of 40% (w/v) acrylamide (AAm, Aldrich), 132 μL of 2% (w/v) bis-acrylamide (Bis, Aldrich), 50 μL of 10% ammonium persulfate (APS, Aldrich) and 2 μL of N',N',N',N'-tetramethylethylene-diamine (TEMED, Aldrich) in DI water. Then, the pre-gel solution was sandwiched and allowed to polymerize between the modified coverslip and unmodified coverslip of 22 mm diameter for 10 minutes at room temperature. After the polymerization, the unmodified cover glass was removed and the poly(acrylamide) (PAAm) gel-coated cover glass was rinsed twice. (2) The surface of PAAm was functionalized with —NHS (-succinimidyl) groups by activating with N-sulfosuccinimidyl-6-[4'-azido-2'-nitrophenylamino] hexanoate (Sulfo-SANPAH, Pierce) in the presence of UV light. UV with 252 nm wavelength was exposed twice for 7 minutes on the Sulfo-SANPAH solution on PAAm. (3) The fluorescent Bovine Serum Albumin (rhodamine-BSA, Aldrich) as a model protein was encapsulated in the PEGDA-MA hydrogel containing microchannels, and the hydrogel was placed on the activated PAAm substrate. The BSA diffuse onto the —NHS (-succinimidyl) groups on the PAAm gel surface during incubation overnight. (4) BSA reacts with —NHS groups to form covalent bonds, and the fluorescence pattern under the PEGDA-MA hydrogel was examined using the fluorescent microscope. b. The diffused BSAs were localized exclusively along circular cross-section of the microchannels with diameter of 500 μm (b-2). Image (b-1) represents the fluorescent image of the rhodamine-BSA encapsulated hydrogel which was captured before incubation, and image (b-2) represents the BSAs localized around the patterned microchannel. c. Validation of diffusion-based model by scaling up while keeping the ratio of R/2H(R; diameter of microchannel, H; thickness of an entire gel) as shown in FIG. 3. For a hydrogel with thickness of 1.0 mm, the model predicted that the diameter of the microchannels should be less than 4.0 mm in order to make $J_m$ larger than $J_f$ in FIG. 3b. As predicted, BSA diffused from the hydrogel containing a channel with diameter of 7.0 mm did not result in any localization of proteins along the channel (c-1) while the hydrogel containing microchannels with diameter of 2.0 mm induced the protein localization.

FIG. 17 a-b shows a schematic representation of in-shell CAM angiogenesis assay. a. Briefly, embryonic chicken eggs (Hy-Line W-36) purchased from the Poultry Research Farm at the University of Illinois (Urbana, Ill.) were incubated at 37° C. with 5% $CO_2$. On the 9th day of gestation, a small window (1.0×1.0 cm) was created on top of each egg. After one day of additional incubation to stabilize CAM and the embryos, a fibroblast-encapsulated hydrogel disk (5-mm diameter, 200-μm thickness) was implanted on top of the CAM. The fibroblast density was kept constant at $5 \times 10^6$ cells/mL. After incubation for seven days, the membrane was fixed with 10% neutral buffered formalin (NBF) for 20 hours. The fixed membrane surrounding the gel structure (10 mm×10 mm) was cut out. A photo in (b) shows the CAM and egg shell used in this study.

FIG. 18 a-d shows a chick embryo chorioallantoic membrane (CAM) angiogenesis assay. Development of capillaries following the implantation of fibroblast-encapsulated hydrogel was monitored by capturing images of CAM with CCD camera on Days 2, 4 and 7. Photos in (a) represents a CAM onto which the fibroblast-encapsulated PEGDA1000 hydrogel was implanted Photos in (b) represents a CAM onto which the fibroblast-encapsulated PEGDA-MA hydrogel without microchannel. Photos in (c) and (d) represent CAM onto which the fibroblast-encapsulated PEGDA-MA hydrogel containing microchannels with diameters of 500 μm or 1,000 μm, respectively. Diameter and thickness of the hydrogel implant were kept constant at 5 mm and 200 μm, respectively. The density of fibroblasts encapsulated in the hydrogel was kept constant at $5 \times 10^6$ cells/ml.

FIG. 19 a-b shows micro-scale neovessel patterns regulated by the microchannel geometry of the cell-encapsulating hydrogel. a. The neovascular patterns were reproducibly formed equivalent to the pattern engraved into the hydrogel stamp with controlled diameters and spacings (scale bar represents 500 μm), except the hydrogel containing microchannels with diameter of 1,000 μm. b. Quantitative analysis of the number ratio of the patterned neovessels to the microchannels was related to the diameter of microchannels, which alters balance between $J_f$ and $J_m$ in the diffusion-model as shown in FIG. 2. The reproducibility of patterning neovessels was evaluated with the ratio of the number of circular-shaped neovessels to that of microchannels. The values of the reproducibility in patterning neovessels for microchannel diameters at 300, 500 and 750 μm were statistically different from for 1,000 μm, according to the statistical analysis. The values of reproducibility represent averaged values from four different samples/CAM assays for each channel size.

FIG. 20 a-b shows a histological analysis of neovessels controlled by microchannel geometry. a. The images show a cross-section of the CAM stained with antibody to α-smooth muscle actin (α-SMA). The mature neovessels were identified with α-SMA layer stained. b. The implantation of hydrogel containing microchannels with diameter of 500 μm (a-1) resulted in a significant increase in the number of mature neovessels marked with α-SMA as compared with the neovessel developed by microchannels with diameter of 1000 μm (a-2). The mature neovessel density for microchannel diameter of 500 μm was statistically different from that for 1,000 μm, according to the statistical analysis.

FIG. 21 a-b shows host inflammation mediated by structural integrity of the fibroblast-encapsulated hydrogel implants. Intact hydrogel minimally stimulated host inflammation (a), while fractured hydrogel stimulated inflammation marked by white fibrous tissues around the implant (indicated by an arrow) within two days (b). Scale bar represents 500 μm.

FIG. 22a shows that implantation of the PEGDA hydrogel did not generate capillary patterns. Rather, it stimulated the inflammation. FIG. 22b shows the patterning of neovessels was not achieved with the PEGDA-MA containing microchannels encapsulating only VEGF (30 ng/ml), rather than fibroblasts.

FIG. 23 a-c shows vascularization activity of the stamp laden with human bone marrow-derived mesenchymal stem cells (hMSCs). a. Viability of hMSCs encapsulated in the microvascular stamp was evaluated using a calorimetric assay that measures metabolic activity. A population of hMSCs survived the stereolithographic process and remained viable within the microvascular stamp for at least 7 days. b. Cellular VEGF secretion level was determined using a human VEGF ELISA kit. The amount of cell-secreted VEGF (■) for five days was 10 times larger than NIH/3T3 cells (●) in the stamp. c. and d. The microvascular stamps implanted on CAM membranes generated blood vessels with the same pattern as the microchannels.

DETAILED DESCRIPTION OF THE INVENTION

Figure 3E:
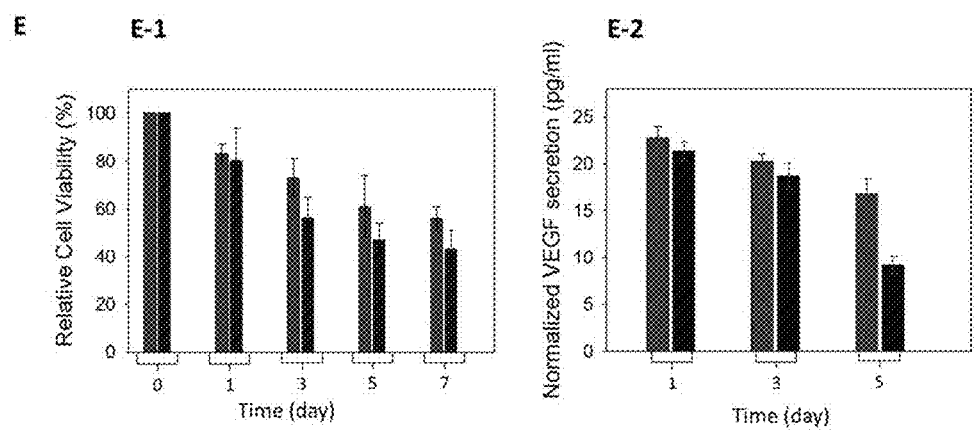
FIG. 3 a-e shows determination of microchannel geometry to direct neovessel growth along circles of the microchannels and introduction of the microchannel into a cell-encapsulating hydrogel using a stereolithographic apparatus (SLA). a. It was hypothesized that the flux of cell-secreted growth factors released through a microchannel wall of a hydrogel ($J_m$) should be larger than that released through the bottom of a gel with the same cross-sectional area as the microchannel ($J_f$) in order to control the growth pattern of neovessels. b. A modeling based on the Fick's law of diffusion suggested that $J_m$ should be larger than $J_f$ as the microchannel diameter becomes smaller than 800 μm with a hydrogel with thickness of 200 μm. c. Following the model-based calculation, microchannels with diameter of 500 μM were incorporated into the hydrogel via the bottoms-up process with SLA. In c, the image represents the fluorescent image of the hydrogel containing fluorophores. d. Water protons imaged with MRI diffused into the PEGDA-MA hydrogel more preferably through the microchannel wall, leading to the faster water diffusion than the microchannel-free hydrogel. e. The fraction of viable NIH/3T3 cells became higher by introducing microchannels into the PEGDA-MA hydrogel (e-1). In (e-1), ▨ bar (right bar) represents the PEGDA-MA hydrogel without microchannel, and ▨ bar (left bar) does the PEGDA-MA hydrogel with microchannels. The amount of VEGF secreted by cells was found to be larger with cells encapsulated within the PEGDA-MA hydrogel with microchannels (▨) (right bar) as compared with those encapsulated within the microchannel-free PEGDA-MA hydrogel (▨)(left bar) (e-2).

As used herein, the singular forms "a," "an," and "the" include plural referents unless the context clearly dictates otherwise.

The invention provides 'living' microvascular stamps that release multiple proangiogenic factors along their predefined micro-sized pattern to engineer the stimulation and spatial organization of neovessels. The stamps comprise live cells that secrete certain factors, e.g., proangiogenic factors, engineered hydrogel matrices that promote cellular expression of the factors, and geometry that controls the flux and flow direction of these growth factors. When implanted, the stamps create a desired pattern of neovessels, where the pattern was engraved into the microvascular stamp. The microvascular stamps are very powerful tools for studying and directing emergent cellular behavior of the vasculature, and further repairing or regenerating neovessels to treat wounds, traumas, tissue defects and various diseases.

Microvascular stamps are capable of releasing multiple proangiogenic growth factors along a pattern engraved into the stamps, while maintaining structural integrity at the implant site, such that a desired vascular pattern is generated. Cells that endogenously express multiple proangiogenic growth factors are encapsulated into a rigid but permeable hydrogel of poly(ethylene glycol) (PEGDA) and methacrylic polymer, such as methacrylic alginate (MA). In this manner, cells are stimulated to release the soluble factors in a sustained and responsive manner. Furthermore, using a stereolithography fabrication unit, microchannels of appropriate diameter and spacing guided by Fick's law of diffusion, can be incorporated into the cell-encapsulating hydrogel, so the flux of growth factors through the walls of the microchannels are much larger than that through other parts of the hydrogel (FIG. 1). The hydrogel permeability can be evaluated by monitoring water diffusion into the hydrogel with magnetic resonance imaging (MRI) (see Example 1), and the function of the microvascular stamp to control neovessel formation can be examined by implanting it onto, for example, a chick embryo membrane (CAM) (see Example 4).

Hydrogel

Hydrogel compositions of the invention comprise poly(ethylene glycol) diacrylate (PEGDA) and methacrylic polymer, (a polymer whose monomer is a methacrylic ester with the general formula $H_2C=C(CH_3)COOR$), such as methacrylic alginate (MA), hyaluronic acid methacrylate, chitosan methacrylate, polyaspartamide methacrylate, hyperbranched polyglycerol methacrylate, glycosaminoglycan methacrylate, Pluronic methacrylate, heparin methacrylates, dextran methacrylates, and combinations thereof. The elastic modulus and swelling ratio of the PEGDA-methacrylic polymer hydrogel are tuned to prepare a rigid and permeable hydrogel, so that the cell-encapsulated hydrogel not only remains stable at the implanted site but also supports cellular expression of factors such as proangiogenic factors.

The elastic modulus of a stamp (with or without cells) can be from about 10 kPa to about 140 kPa (or any range or value between about 10 kPa to about 140 kPa), for example from about 20 kPa to about 120 kPa. The swelling ratio of a hydrogel (with or without cells) can be from about 25 to about 10 (or any range or value between about 25 and 10), for example, from about 20 to about 12.

The amount of methacrylic polymer in a hydrogel composition of the invention can be about 2.5% (w/w) to about 10.0% (w/w) (or any range or value from about 2.5% to about 10.0%). The amount of PEGDA in a hydrogel composition of the invention can be about 12.5% (w/w) to about 17.5% (w/w) (or any range from about 12.5% to about 17.5%). The molecular weight of the PEGDA can be about 700 g/mol to about 10,000 g/mol (or any range or value between about 700 g/mol and about 10,000 g/mol). The ratio of PEGDA to methacrylic polymer can be about 1:10, 2:10, 3:10, 4:10, 5:10% (w/w) (or any range or value between about 1:10 and about 5:10% (w/w), e.g., about 2.5:10% (w/w)).

The diffusity of a stamp with no microchannels can be from about $1.0\times10^{-8}$ $cm^2/s$ to about $3.0\times10^{-8}$ $cm^2/s$ (or any range or value between about $1.0\times10^{-8}$ $cm^2/s$ to about $3.0\times10^{-8}$ $cm^2/s$), for example, from about $1.2\times10^{-8}$ $cm^2/s$ to about $2.6\times10^{-8}$ $cm^2/s$.

The diffusity of a stamp with microchannels can be from about $1.0\times10^{-8}$ $cm^2/s$ to about $3.5\times10^{-8}$ $cm^2/s$ (or any range or value between about $1.0\times10^{-8}$ $cm^2/s$ to about $3.5\times10^{-8}$ $cm^2/s$), for example, from about $1.5\times10^{-8}$ $cm^2/s$ to about $3.14\times10^{-8}$ $cm^2/s$.

The thickness of a stamp can be from about 100 μm to about 5 mm (or any range or value between about 100 μm to about 5 mm), for example, from about 100 μm to about 500 μm.

In relation to the stamp parameters discussed above, the diameter and spacing of microchannels, and neovessel spacing and length, the term "about" means that the stated parameter value can vary by 5% or less.

In contrast to conventional two-dimensional cell culture systems (flat 2D surfaces such as membranes, culture dishes, or multi-well tissue culture plates where cells grow in monolayers), the microvascular stamps mimic the complex three-dimensional cellular structure of living tissues by providing an adhesive substrate for cells and by acting as a three-dimensional physical, porous support for cells in culture and in vivo.

A stamp can be in a variety of shapes including sheets, slabs, cylinders, tubes, spheres, or beads. A stamp can also be provided in a shape that provides natural contours of a body part, e.g., a nose or nose part, an ear or ear part, a meniscus, etc.

Encapsulation of Cells in a Hydrogel

Cells that are known to endogenously express growth factors, antiangiogenic, proangiogenic factors[15], or other factors of interest are encapsulated into the PEGDA and PEGDA-methacrylic polymer hydrogels. The mixture of cells and pre-gelled methacrylic polymer, PEGDA and a photoinitiator (e.g., Iragacure 2959) solution can be exposed to UV light or a laser (e.g., a laser of a stereolithography fabrication apparatus) to activate in situ photo cross-linking reaction to form a hydrogel[18] (FIGS. 10 & 11) (see Example 1). Cells encapsulated into a PEGDA-methacrylic polymer hydrogel remain more viable than those encapsulated into a PEGDA hydrogel, regardless of the gel stiffness (FIG. 2c and FIG. 13) (see Example 2). The beneficial role of PEGDA-methacrylic polymer hydrogel in enhancing cell viability may be attributed to its increased permeability and subsequently higher water diffusivity (FIG. 2b & FIG. 2c) (see Example 1).

Cell density in a hydrogel can be from about $1 \times 10^2$ to about $1 \times 10^8$ cells/ml (or any range or value between about $1 \times 10^2$ to about $1 \times 10^8$ cells/ml), for example about $2 \times 10^6$ cells/ml. In one embodiment of the invention, the cells are uniformly distributed throughout the hydrogel. In other embodiments, the cells can be distributed in a gradient. That is, one or more portions of the hydrogel can have a greater cell density than one or more other portions of the hydrogel. The different densities can be achieved using a bottoms-up approach of SLA wherein different densities of cells are present in each layer (see Example 2).

Cells encapsulated within the PEGDA-methacrylic polymer hydrogel can express larger amounts of multiple proangiogenic or growth factors than those encapsulated in a PEGDA hydrogel. Proangiogenic factors and growth factors include, e.g., vascular endothelial growth factor (VEGF) (A-F), proliferin, serpin E1, endothelin-1, fibroblast growth factors (acidic and basic FGF 1-10), granulocyte-macrophage colony-stimulating factor (GM-CSF), insulin, insulin growth factor or insulin-like growth factor (IGF), insulin growth factor binding protein (IGFBP), placenta growth factor (PlGF), angiopoietin (Ang1 and Ang2), platelet-derived growth factor (PDGF), hepatocyte growth factor (HGF), transforming growth factor (TGF-α, TGF-β, isoforms 1-3), platelet-endothelial cell adhesion molecule-1 (PECAM-1), vascular endothelial cadherin (VE-cadherin), nitric oxide (NO), chemokine (C—X—C motif) ligand 10 (CXCL10) or IP-10, interleukin-8 (IL-8), hypoxia inducible factor (HIF), monocyte chemotactic protein (MCP), such as MCP-1, vascular cell adhesion molecule (VCAM), ephrin ligands (including Ephrin-B2 and -B4); transcription factors including HIF-1α, HIF-1β and HIF-2α, Ets-1, Hex, Vezf1, Hox, GATA, LKLF, COUP-TFII, Hox, MEF2, Braf, Prx-1, Prx-2, CRP2/SmLIM and GATA family members, basic helix-loop-helix factors and their inhibitors of differentiation; and regulatory molecules including enzymes (matrix metalloproteinase (MMP) such as MMP-9, tissue plasminogen activator (PLAT or tPA), and cyclooxygenase (COX) or angiogenin.

For example, the amount of cell-secreted VEGF was much larger for cells encapsulated within a PEGDA-methacrylic polymer hydrogel as compared with those encapsulated within a PEGDA hydrogel. See Example 2.

In certain embodiments, cells can express one or more antiangiogenic factors such as endoglin, fms-like tyrosine kinase 1 (sFlt1), NRP-1, IFN-α, IFN-β, IFN-γ, CXCC10, IL-4, IL-12, IL-18, prothrombin, maspin, angiostatin, endostatin, TSP-1, TSP-2, vasostatin, platelet factor 4, or prolactin.

Cells encapsulated into a hydrogel can be any type of cells such as a stem cell a human embryonic stem cell, a mesenchymal stem cell, a bone marrow-derived mesenchymal stem cell, a human bone marrow-derived mesenchymal stem cells a hematopoetic stem cell, a blood stem cell, an adult stem cell, an embryonic stem cell, a post-natal stem cell, a fetal cardiomyocyte, an endothelial progenitor cell, circulating angiogenic cells, circulating endothelial precursors, endothelial colony-forming cells, early outgrowth endothelial progenitor cells, late outgrowth endothelial progenitor cells, a cord blood stem cell, an autotransplanted expanded cardiomyocyte, a cardiomyocyte, a cardiac myoblast, a myofibroblast, a fibroblast, an adipocyte, a totipotent cell, a pluripotent cell, a multipotent mesenchymal stem cell, a synovial cell, a spinal disc cell, a tenocyte, a myoblast, a bone marrow cell, a mesenchymal cell, a parenchymal cell, an epithelial cell, an endothelial cell, a mesothelial cell, a fibroblast, a myofibroblast, an osteoblast, a chondrocyte, an exogenous cell, an endogenous cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell, a unipotent progenitor cell, a monocyte, a skeletal myoblast, a macrophage, a capillary endothelial cell, a xenogenic cell, and an allogenic cell. One type of cell or a combination of two or more types of cells can be encapsulated in a hydrogel of the invention.

The cells can be human, adult human, infant human, fetal human, juvenile human, mammalian, equine, bovine, murine, feline, canine, porcine or any other type of cells.

After encapsulation, the cells can be stimulated to secrete growth factors or other proangiogenic factors with, for example, stimulation factors such as protein kinase C activators (e.g., TPA), oxygen concentration, external mechanical forces, light, or heat. The stimulation factors can be added prior to formation of the hydrogel, after formation of the hydrogel, prior to implantation or grafting of the stamp, during implantation or grafting of the stamp, after implantation or grafting of the stamp, or a combination thereof.

In one embodiment of the invention cells release growth factors, proangiogenic factors, or antiangiogenic factors upon specific environmental stimulation such as exposure to a certain wavelength of light, change in temperature, change in oxygen concentration, or change in pressure. In one embodiment of the invention a protein of interest (e.g., one or more growth factors, proangiogenic factors, or antiangiogenic factors or precursors of these factors) is fused to a protein light switch, such that illumination of the fusion protein activates or inactivates the protein of interest. The activation or inactivation can be reversible, that is, the activation or inactivation is not permanent. The activation can be dose dependent that is, increased illumination increases the level of activation or inactivation of the protein of interest. The illumination can comprise any wavelength that modulates a protein light switch, for example, light in the range of about 450 to about 500 nm, More than one wavelength of light can be used for illumination.

A protein light switch can be any protein or peptide that is responsive to illumination such that it that changes structure in response to illumination. A protein light switch can be a LOV (light, oxygen or voltage) domain, such as a LOV2 domain, or a portion thereof that retains substantially all of the responsiveness to illumination, See, Toettcher et al., Nature Methods, 8:35 (2011); Strickland et al., Nature Methods, 7:623 (2010). Examples of LOV domains are taught in e.g., Pathak et al., Photochem. Photobiol. 88:107 (2012); Herrou & Crosson, Nat. Rev. Microbiol. 9:713

(2011). A protein light switch can further comprise a Jα domain and/or one or more fragments from a phototropin, e.g., phototropin I. See WO2011/002977.

Cells of the invention can be engineered to express one or more the fusion proteins comprising one or more of the proteins of interest and a protein light switch using methods know to one of skill in the art. See WO2011/002977. In the absence of certain light wavelengths, a LOV domain will sterically block or perturb the protein function in cells. However, upon exposure to certain light wavelengths the block on protein function is released. In this manner cells within the microvascular stamp can be controlled via light to express and release growth factors, proangiogenic factors, or antiangiogenic factors at specific times. Removal of the light again blocks the protein function such that the proteins are not expressed and released.

Therefore, a microvascular stamp can be illuminated with light while the stamp is in vitro for, e.g., experimental purposes, prior to implantation into a subject, during implantation into a subject, and/or while the stamp is implanted in a subject. A stamp can be illuminated constantly, at one time point, or at several time points. Illumination can last for about 0.5, 1, 5, 10, 30 minutes or more at each time point.

Microchannels

Microchannels can be incorporated into a microvascular stamp through, e.g., in situ cross-linking reactions activated by a sterolithographic assembly (SLA) unit. See e.g., Example 1. Microchannels with controlled spacing can be introduced into the PEGDA-methacrylic polymer hydrogels with the goal of driving neovessel growth along the microchannel pattern. Neovessel growth direction can be controlled by increasing the flux of the cell-secreted proangiogenic factors through the microchannel wall, so that the neovessels localize within the microchannel lumen. The ratio between the flux of growth factors through the microchannel wall of the stamp ($J_m$) should be larger than the flux through the bottom of the stamp with the same cross-sectional area as the microchannel ($J_f$) (see Example 3).

The microchannels can be about 100 µm to about 2.5 mm in diameter (or any range or value from about 100 µm to about 2.5 mm in diameter), for example about 200 µm to about 2.0 mm in diameter. The on-center spacing between the microchannels can be about 100 µm to about 2.5 mm (or any range or value from about 100 µm to about 2.5 mm), for example from about 200 µm to about 2.0 mm. On-center spacing is the center to center measurement from one microchannel to the next.

In one embodiment of the invention all microchannels in the stamp have the same on-center spacing. In another embodiment of the invention, the on-center spacing can be different between two or more of the microchannels. The microchannels can be any shape, for example, the shape can be circles, squares, triangles, random shapes, or a mixture of shapes (see e.g., FIG. 23 d). The microchannels can be arranged randomly or can be in a pattern (e.g., a set of repeating microchannels at predetermined positions). A microchannel pattern can regulate the local distribution of proangiogenic factors on an implantation or graft site.

Microchannels can be fabricated in the hydrogels using a stereolithographic apparatus (SLA)[18]. Incorporation of the microchannels into the hydrogel make minimal difference in the elastic modulus and swelling ratio as compared to the microchannel-free hydrogel. The diffusivity (D) of water into the PEGDA-methacrylic polymer hydrogel is significantly increased due to the presence of microchannels. Water diffuses into a hydrogel more exclusively through microchannel walls and ultimately leads to a faster increase in the amount of water bound to the gel matrix than the microchannel-free hydrogels. Incorporation of the microchannels into the hydrogel also increases the fraction of viable cells due to increased chances of nutrient and waste exchange over time. In addition, incorporation of the microchannels into PEGDA-methacrylic polymer hydrogels improves sustainability of secreting proangiogenic factors during cell culture.

Therefore, a microvascular stamp can be made by a method comprising encapsulating cells in a PEGDA and methacrylic polymer hydrogel; crosslinking the hydrogel with a stereolithographic apparatus (or other suitable composition or method) to form a cross-linked hydrogel; and incorporating microchannels into the cross-linked hydrogel with a stereolithographic apparatus (or other suitable composition or method), such that a microvascular stamp is made. The microvascular stamp can then be contacted with a tissue in vivo or in vitro.

Compositions

Compositions of the invention include a microvascular stamp comprising one or more types of cells encapsulated in a poly(ethylene glycol) (PEGDA) and methacrylic polymer cross-linked hydrogel, wherein the cross-linked hydrogel comprises microchannels. A stamp can be populated with neovessels. That, is one or more neovessels are present within the stamp. The one or more types of cells express one or more fusion proteins comprising a growth factor, proangiogenic factor, or antiangiogenic factor fused to a protein light switch.

Microvascular stamps of the invention can be used for tissue regeneration. Alternatively, microvascular stamps of the invention can be used for in vitro studies, e.g., to study neovessels, to study cell attachment, gene expression, cell contraction, cell motility, etc.

Optionally, a microvascular stamp of the invention can be used without encapsulated cells. In this case one or more proangiogenic factors or growth factors (e.g., VEGF, FGF, endothelin, proliferlin) would be added to the microvascular stamp (during the pre-gel phase, or after formation of the hydrogel is completed).

Kits of the invention can include a microvascular stamp in medium suitable for retaining viability of the encapsulated cells. Optionally, a delivery device such as a syringe, catheter or forceps can be included in the kit. Other kits of the invention can comprise one or more of a pre-gel solution of methacrylic polymer and PEGDA, cells, cell stimulator, a photoinitiator or combinations thereof.

Methods of Use

One embodiment of the invention provides a method for stimulating neovessels and controlling spatial organization of neovessels in vitro or in a subject having a disorder characterized by tissue damage or loss comprising implanting or grafting a stamp of the invention in or on the subject. The neovessels are functional, that is, blood flows in the neovessels.

For example, a microvascular stamp of the invention, which has one or more cell types encapsulated within it, can be implanted into or grafted onto a subject or tissue culture such that formation of neovessels is induced. The neovessels can be about 100 µm to about 2.5 mm apart from one another and about 10 to about 1,000 µm long (or any range or value between about 10 to about 1,000 µm long, such as about 100 to about 500 µm long).

In one embodiment of the invention, a method of inducing growth of new blood vessels in a tissue in vitro or in vivo is provided. The method comprises contacting one or more microvascular stamps of the invention with the tissue, wherein the microvascular stamp induces the growth of new blood vessels. The microscale spacing between functional new blood vessels can be controlled by controlling the size or diameter, shape and spacing of the microchannels in the microvascular stamp. The microscale spacing between the new blood vessels can be about 100 µm to about 2.5 mm on-center.

In another embodiment of the invention, a method of treating a tissue defect in a subject in need thereof is provided. The method comprises administering one or more of the microvascular stamps of the invention to the subject, thereby treating the tissue defect. A microvascular stamp of the invention can be administered to a subject by any suitable method, including, for example, injection, implantation, endoscopic delivery, or by catheter.

Microvascular stamps of the invention can be used as, e.g., grafts for dermal wounds, pressure sores, venous stasis wounds, diabetic ulcers, and/or reconstructive applications. Microvascular stamps of the invention can also be used to treat a disorder characterized by tissue damage or loss or in need of neovascularization. A disorder characterized by tissue damage or loss includes any disorder, disease or condition comprising tissue damage or trauma (e.g., non-functional tissue, cancerous or pre-cancerous tissue, broken tissue, fractured tissue, fibrotic tissue, or ischemic tissue) or a tissue loss (e.g., due to trauma, infectious disease, genetic disease, or other disease) that would benefit from neovessel stimulation and generation. Examples of disorders or conditions requiring neovascularization include liver cirrhosis, ischemia, diabetes, cystic fibrosis, bone cancer, bone damage, burns and wounds, age related macular degeneration, myocardial infarction, myocardial damage, heart valve damage, CNS lesions, nerve damage, peripheral nerve damage, spinal cord defects, articular cartilage defects, urological organ damage or degeneration, intestinal damage or degeneration, conjunctiva damage, bone and tendon interface damage or degeneration, cartilage damage, pancreatic tissue damage, liver tissue damage, and osteochondral defects.

Where cells are encapsulated into the stamp (including, for example, for ex vivo formation of a tissue) the cells can be derived from the treated subject (autologous source), from allogeneic sources such as embryonic stem cells that are not expected to induce an immunogenic reaction, from xenogeneic sources, or combinations thereof.

In any of these methods the one or more types of cells in the stamp can express one or more fusion proteins comprising a growth factor, proangiogenic factor, or antiangiogenic factor fused to a protein light switch. The one or more microvascular stamps can then be illuminated with light at a wavelength of about 450 nm to about 500 nm to cause the expression of the growth factor, proangiogenic factor, or antiangiogenic factor in the fusion protein.

A therapeutically effective amount of a stamp of the invention is an amount of a microvascular stamp composition in sufficient strength such that the composition has a positive effect on the neovascularization of tissue that is being treated in the subject. The amount is therapeutically effective where the composition has an effect on the regenerative or wound healing activity at the site where the composition contacts tissue. A therapeutically effective amount can be determined by routine testing in patients with wounds or tissue defects.

A microvascular stamp can remain at the treatment site until the desired result is achieved (e.g., wound healing). After the desired result is achieved, the stamp can be removed. The duration of a microvascular stamp of the invention is the length of time required for the stamp to for example, give the cells or tissues within the stamp time to function to, for example regenerate skin at a wound site. The duration of a stamp can be about 1 day, 2 days, 3 days, 4 days, 5 days, 6 days, 7 days, 10 days, 2 weeks, 3 weeks, 4 weeks, 5 weeks, 6 weeks, 7 weeks, 8 weeks, 3 months, 4 months or more.

Optionally, a microvascular stamp can be populated or partially populated with neovessels in vitro and then the stamp can be implanted or grafted into a subject as described above.

All patents, patent applications, and other scientific or technical writings referred to anywhere herein are incorporated by reference herein in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above.

EXAMPLES

Example 1

Hydrogel Preparation

Gel-forming polymers, poly(ethylene glycol) diacrylate (PEGDA) and methacrylic alginate (MA), were synthesized as described in FIG. 6 and our previous works[16]. Briefly, for the synthesis of MA, 2-Aminoethylmethacrylate was conjugated to the carboxylate group of alginate via EDC chemistry. See FIG. 6a. The alginate used in this experiment (molecular weight ($M_w$)~50,000 g/mol) was obtained by irradiating alginate rich in gluronic acid residues, (LF20/40, FMC Technologies, $M_w$~250,000 g/mol) with a dose of 2 Mrad for 4 hours from a $^{60}$Co source. The irradiated alginate was dissolved in the 0.1M MES ((2-(N-morpholino) ethanesulfonic acid) buffer (pH 6.4, Sigma-Aldrich) at the concentration of 1.0% (w/v). Then, 1-hydroxybenzotriazole (HOBt, Fluka), 1-ethyl-3-(3-dimethylaminopropyl) carbodiimide (EDC, Thermo Scientific) and 2-aminoethyl methacrylate (AEMA, Sigma Aldrich) were dissolved in the alginate solution and stirred for 18 hours. Both the molar ratio of HOBt to AEMA and the molar ratio of EDC to AEMA were kept constant at 2:1. The mixture was dialyzed extensively against deionized (DI) water for three days, while exchanging the DI water every 12 hours. The dialyzed alginate solution was lyophilized, and reconstituted to a 3 wt % stock solution. The conjugation of methacrylate groups onto the alginate was confirmed by $^1$H-NMR (300 MHz, QE300, General Electric), as previously reported.

In parallel, PEGDA was synthesized via chemical reaction between poly(ethylene glycol) (PEG, Sigma Aldrich) and acryloyl chloride (Sigma Aldrich). See FIG. 6b. First, PEG was dissolved in dichloromethane at the concentration of 10 wt %. Next, acryloryl chloride and triethylamine (Fisher Chemical) were dissolved in the PEG solution and stirred overnight under dry $N_2$ gas. The molar ratio of PEG, acryloyl chloride and triethylamine was 1:4:4. Finally, the insoluble salt (triethylamine-HCl) was filtered, and the product was precipitated by adding ice-cold ether. The crude product was dissolved into DI water and dialyzed for one day to remove unreacted starting materials and the salt, a byproduct. Then, the product was frozen at −20° C. and lyophilized. The conjugation of acrylate groups onto PEG was confirmed by $^1$H-NMR (300 MHz, QE300, General Electric). In this study, the number of methacrylates linked to a single alginate with molecular weight ($M_w$) of 50,000 g/mol was kept constant at 60. The PEGDA with $M_w$ of 1,000 g/mol and MA were dissolved in Dulbecco's modified Eagle's medium (DMEM, Sigma Aldrich) without phenol red as stock solutions. The concentration of PEGDA in the stock solution and that of MA were kept constant at 40° A) w/v and 3.0% w/v, respectively.

The pre-gelled solution was made by mixing 2.0 mL of the PEGDA solution with varied amounts of MA while keeping the total gel-forming polymer concentrations constant (FIG. 2). The mixture of pre-gelled solution was further mixed with 0.2 wt % of the photoinitiator (Irgacure 2959, Ciba). The pre-gelled solution was subsequently exposed to UV light or laser of stereolithographic apparatus (SLA) to activate photo cross-linking reaction to form the hydrogel. See FIG. 7.

Where SLA was used, the pre-gelled solution was placed into the dish at the center of the platform in SLA. A commercially-available SLA was modified to accommodate for the bottoms-up approach developed in our previous work[19] (FIG. 10). Briefly, the hydrogel with microchannels was fabricated by photo crosslinking the mixture of cell and pre-gelled solution in a layer by layer fashion using a stereolithography apparatus (SLA, Model 250/50, 3D Systems). A commercially-available SLA was modified to accommodate for the bottoms-up approach as describe in our previous work[15]. In the bottoms-up approach, the pre-gelled solution is pipetted into the container one layer at a time from the bottom to the top. Each layer is about 100 to about 200 µm. This setup was designed to reduce total volume of photopolymer in use and also remove photopolymers used from static conditions.

3D computer-aided design (CAD) models were generated using AutoCAD 2009 (Autodesk) and exported to stereolithography (SLA) format for creating hydrogels containing microchannels (FIG. 12). The microchannels with varied diameters were introduced into hydrogels guided by the following Fick's diffusion equation[24-25].

$$J_s = P \times S \times (C_i - C_o) \quad \text{(Eq. 1)}$$

where $J_s$ is the diffusive flux of a molecule, P is the hydrogel permeability coefficient, $C_i$ and $C_o$ are the molecule concentrations in and out of a hydrogel, and S is the surface area of a hydrogel.

The SLA software, 3D Lightyear v1.4 (3D system), was used to slice the 3D models into a series of 2D layers from a user-specified thickness. The laser was used to selectively crosslink the pre-gelled solution at a precisely calculated energy dose (FIG. 11). The elevator controlled by the SLA was lowered by a specified distance, and the part was recoated. The process was repeated until completion of the 3D assembly of the hydrogel. The hydrogel was rinsed several times in the phosphate buffered saline (PBS, pH 7.4) to remove uncross-linked polymer, and the gel was further incubated in the medium for 24 hours at 37° C.

Hydrogel Characterization.

The hydrogel stiffness was evaluated with measurement of the elastic modulus of a hydrogel. Following the incubation in the medium for 24 hours, the gel structure was compressed at a rate of 1.0 mm/min using a mechanical testing system (MTS Insight). The elastic modulus was calculated from the slope of a stress (a) vs. strain (A) curve at the first 10% strain. The hydrogel swelling ratio at equilibrium was determined by measuring the weight of the hydrated gel after 24 hours in neutral buffered solution at 37° C. and that of the dried gel. The degree of swelling (Q), defined as the reciprocal of the volume fraction of a polymer in a hydrogel ($v_2$), was calculated from the following equation, $$Q = v_2^{-1} = \rho_P \left[ \frac{Q_m}{\rho_S} + \frac{1}{\rho_P} \right] \quad \text{(Eq. 2)}$$

where $\rho_S$ is the density of water, $\rho_P$ is the density of polymer, and $Q_m$ is the mass ratio of swelled gel to the dried gel.

Magnetic Resonance Imaging (MRI).

Water diffusion into a hydrogel was examined by measuring the local amount of water proton in the hydrogel with the magnetic resonance imaging (MRI). MRI was carried out using 600 MHz Varian Unity/Inova nuclear magnetic resonance (NMR) spectrometer (14.1 T Magnet) at room temperature. Each gel disk (5 mm in diameter, 1 mm in thickness) was incubated in PBS at room temperature during certain time periods. Then, the gel was moved into a glass bottle (20 mm in diameter, 40 mm in height), then inserted into a RF (Radio Frequency) coil. Spin echo multi-slice (SEMS) pulse sequence was used to acquire resonance data, which were then converted into water density map using VNMR 6.1C software[26]. For SEMS pulse sequence, the repetition time ($T_R$) of 2.5 s and the echo time ($T_E$) of 5 ms were used. The field of view (FOV) was 1.6×1.6 cm, and the image matrix was 128×64 pixels. The resulting water density images were processed to present the density spectrum for comparison using MATLAB (The Mathworks™). For visualization, pseudo-color was added to the images using the ImageJ software (free image analysis software from National Institutes of Health). For counting water intensity peaks, the rectangular gel picture from the image was selected, and the histogram of the image (count vs. color intensity) was taken using the ImageJ software. The amount of water in a hydrogel was calculated by integrating the histogram for the color intensity higher than 150. The following equation was used to calculate the diffusivity (D) for $W_t/W_\infty < 0.8$, where t is the time and L is the initial thickness of the gel[27].

$$\frac{W_t}{W_\infty} = \frac{4}{\sqrt{\pi}} \times \left( \frac{D \times t}{L^2} \right)^{1/2} \quad \text{(Eq. 3)}$$

CONCLUSION

Firstly, the elastic modulus and swelling ratio of the poly(ethylene glycol) diacrylate (PEGDA) hydrogel were tuned to prepare a rigid and permeable hydrogel, so that the cell-encapsulated hydrogel would not only remain stable at the implanted site but also support cellular expression of proangiogenic factors. Increasing the total polymer concentration of the PEGDA hydrogel showed an increase in elastic modulus and a decrease in swelling ratio, which is the typical inverse relationship between stiffness and bulk permeability of conventional hydrogel systems (FIG. 2a). In contrast, the hydrogel comprising PEGDA and synthetic methacrylic alginate (MA) which presents multivalent methacrylic groups and hydrophilic hydroxyl groups[16] showed an increase in both elastic modulus and swelling ratio with the mass fraction of MA (FIG. 2a). The role of MA in increasing the swelling ratio of the hydrogel was further examined by monitoring the diffusion of water protons into the hydrogel using magnetic resonance imaging (MRI). Despite the higher stiffness of the PEGDA-MA hydrogel compared to the PEGDA hydrogel, water diffused into the PEGDA-MA hydrogel more rapidly (FIG. 2b & FIG. 8).

This was also confirmed by calculating the diffusivity using Eq. (3), which was found to be $2.6 \times 10^{-8}$ $cm^2/s$ for PEGDA-MA and $1.2 \times 10^{-8}$ $cm^2/s$ for PEGDA hydrogel.

Example 2

Cell Encapsulation

NIH/3T3 cells (ATCC) were expanded and passaged at 37° C. with 5% $CO_2$ in Dulbecco's modified Eagle's medium (DMEM, ATCC) supplemented by 10% fetal bovine serum (FBS, ATCC), and 1% penicillin/streptomycin (ATCC). All the cells before the passage number of 10 were used in this study. Prior to encapsulation in hydrogels, cells were mixed with the pre-gelled polymer solution. The cell density was kept constant at $2.0 \times 10^6$ cells/ml. The mixture of cell and pre-gelled solution was exposed to the laser of SLA to activate hydrogel formation. (FIG. 13). NIH/3T3 cells cultured for seven days while being encapsulated within hydrogels. A uniform distribution of cells was achieved throughout the hydrogel by the bottoms-up approach of SLA. FIG. 13a. The viability of encapsulated cell was evaluated by adding 0.1 mL of a growth medium and 0.01 mL of MTT (3-(4,5-dimethylthiazol-2-yl)-2,5-diphenyltetrazolium bromide) reagent (ATCC) into a well of a 96-well plate which contained each gel structure. Following the addition of MTT reagent, the medium was incubated for four hours at 37° C. with 5% $CO_2$ while being gently shaken. Live cells (stained as dark purple) in the hydrogels were imaged using a CCD camera (Leica D-LUX 3) mounted on an inverted microscope (Leica DMIL). FIG. 13b. The live cell fraction was further quantified by adding 0.1 mL of a MTT detergent solution (ATCC) to each well and further incubating at 37° C. overnight to dissolve the dark purple product. The gel structure was removed from each well, and the absorbance of the surrounding medium at 570 nm was measured using a microplate absorbance reader (Synergy HT, Biotek). Image (1) (dark purple in live cells) represents cells encapsulated in the PEGDA1000-MA hydrogel containing microchannels with diameter of 500 μm, image (2) for PEGDA1000-MA hydrogel without microchannels, and image (3) for pure PEGDA1000 hydrogel. Arrow in the image (1) indicates the microchannels. FIG. 13.

The cell-hydrogels were incubated in DMEM supplemented by 10% fetal bovine serum (FBS), while changing the media every two days. On Days 0, 1, 3, 5, and 7, viability of cells encapsulated into the hydrogel was quantitatively evaluated using a MTT [(3-(4,5-dimethylthiazol-2-yl)-2,5-diphenyltetrazolium bromide) reagent (ATCC)] assay kit. The cell-hydrogel construct was incubated in the media containing MTT reagent for 4 hours, and the absorbance of the sample altered with the positive staining of viable cells was subsequently measured at 570 nm using a microplate absorbance reader (Synergy HT, Biotek). The absorbance was normalized to the absorbance read at day 0 to quantify the relative cell viability (%).

The encapsulated cells were stimulated to secret growth factors by adding 0.2 mL of DMEM and 100 ng/ml of 12-O-Tetradecanoylphorbol-13-actate (TPA, ATCC) reagent into a well of a 96-well plate which contains each cell-encapsulating gel[17]. For control experiment, cells adhered to a poly(styrene) cell culture plate were also exposed to the same does of TPA. After incubating the cell-hydrogel construct for 24 hours, 100 μl of cell culture media was mixed with a cocktail of biotinylated detection antibodies, and incubated overnight with the proteome profiler mouse angiogenesis array (R&D Systems). The array membrane was washed to remove unbound material and streptavidin-Fluor® (430) conjugates (Invitrogen) and positively stained spots were imaged using a Phosphor Imager (Bio-Rad). In addition, on Days 1, 3, and 5, the amount of VEGF secreted by cells was quantitatively evaluated by the sandwich enzyme immunoassay technique using the mouse VEGF Immunoassay kit (R&D Systems). The sample containing VEGF was pipetted into a well where a polyclonal antibody specific for mouse VEGF has been pre-coated, and incubated for 2 hours. After washing away any unbound substances, an enzyme-linked polyclonal antibody specific for mouse VEGF was added to the well. The enzyme reaction yielded a blue-colored product, and the color intensity was measured using a microplate absorbance reader (Synergy HT, Biotek). The measured value was converted to the amount of VEGF using a calibration curve. The amount of VEGF was further normalized by the number density of cells initially encapsulated into each hydrogel.

Subsequently, fibroblasts that are known to endogenously express proangiogenic factors[15] were encapsulated into the PEGDA and PEGDA-MA hydrogels. The mixture of cells and pre-gelled solutions were exposed to the laser of the stereolithography fabrication apparatus to activate in-situ photo cross-linking reaction[18] (FIGS. 10 & 11). Interestingly, cells encapsulated into the PEGDA-MA hydrogel remained more viable than those encapsulated into the PEGDA hydrogel, regardless of the gel stiffness (FIG. 2c and FIG. 13). The beneficial role of PEGDA-MA hydrogel in enhancing cell viability could be attributed to its increased permeability and subsequently higher water diffusivity (FIG. 2b & FIG. 2c).

Figure 14:
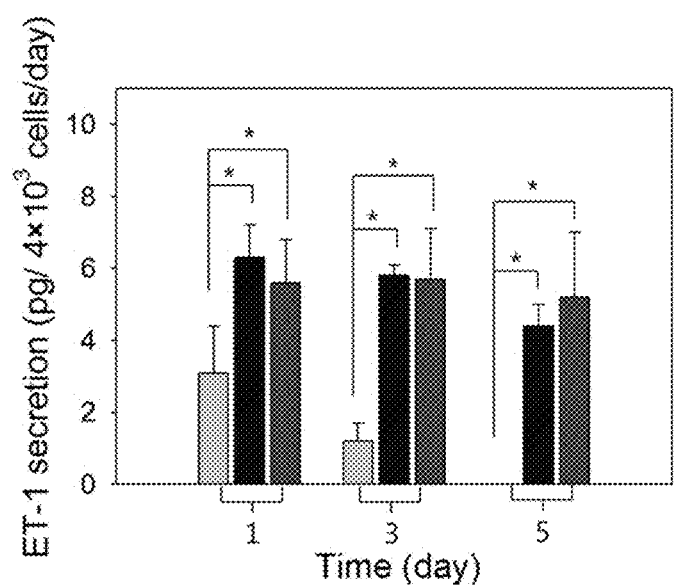
FIG. 14 shows the cellular secretion level of Endothelin-1 on Days 1, 3, and 5, which was measured using the mouse Endothelin-1 (ET-1) Immunoassay kit (Enzo Life Sciences). The cells encapsulated within the PEGDA-MA hydrogels without microchannels (■) (middle bar) and with microchannels (▨) (right bar) expressed the larger amount of endothelin-1 than those within the PEGDA hydrogel (▧) (left bar). The value of ET-1 secretion for the PEGDA-MA hydrogel and for the PEGDA-MA hydrogel with microchannels was statistically different, as compared with that for the PEGDA hydrogel (*$p<0.05$).

In parallel, effects of matrix properties on cellular expression of proangiogenic factors were examined using the fibroblast-encapsulated hydrogels. As revealed by the microarray analysis, fibroblasts encapsulated within the PEGDA-MA hydrogel expressed larger amounts of multiple proangiogenic factors, including vascular endothelial growth factor (VEGF), proliferin, matrix metalloprotein (MMP)-9, monocyte chemotactic protein-1 (MCP-1), Serpin E1 and Endothelin-1 (FIG. 2d), as compared with cells adhered to a 2D poly(styrene) substrate (FIG. 14). Besides, the amount of cell-secreted VEGF was much larger for cells encapsulated within the PEGDA-MA hydrogel as compared with those encapsulated within the PEGDA hydrogel (FIG. 2d).

Example 3

Microchannels

Next, microchannels with controlled spacing were introduced into the PEGDA-MA hydrogels with the goal of driving neovessel growth along its circular pattern (FIG. 12). Neovessel growth direction can be controlled by increasing the flux of the cell-secreted proangiogenic factors through the microchannel wall, so that the neovessels localize within the microchannel lumen (FIG. 3a). According to Fick's law of diffusion (Eq. (1) above), the ratio between the flux of growth factors through the microchannel wall of the stamp ($J_m$) and the flux through the bottom of the stamp with the same cross-sectional area as the microchannel ($J_f$) is equal to the ratio between the surface area of microchannel wall ($S_{wall}$) and the cross-sectional area of the microchannel ($S_{bottom}$). Hence, for a hydrogel with thickness of 200 μm, it could be predicted that the diameter of the microchannels should be less than 800 μm in order to make $J_m$ larger than $J_f$.

Based on this prediction, microchannels with diameter (d) of 500 μm were fabricated in the PEGDA and PEGDA-MA hydrogels using the stereolithographic apparatus (SLA)[18] (FIG. 3c & FIG. 12). A bottom-up fabrication process that has was used to minimize sedimentation of cells during the fabrication process[19]. Incorporation of the microchannels into the hydrogel made minimal difference in the elastic modulus and swelling ratio as compared to the microchannel-free hydrogel. Therefore, the original diameter of the microchannels was minimally altered during the in vivo incubation, regardless of which gel-forming polymers were used (FIG. 13). However, the diffusivity (D) of water into the PEGDA-MA hydrogel as calculated from MRI images (Eq. 3) was significantly increased due to the presence of microchannels (D~$3.14 \times 10^{-8}$ cm$^2$/s) (FIG. 3d & FIG. 9). Interestingly, the MRI images showed that water diffused into the hydrogel more exclusively through microchannel walls and ultimately led to a faster increase in the amount of water bound to the gel matrix than the microchannel-free hydrogels (FIG. 3d). Incorporation of the microchannels into the hydrogel further increased the fraction of viable cells due to increased chances of nutrient and waste exchange over time (FIG. 3e). In addition, incorporation of the microchannels into the PEGDA-MA hydrogel further improved sustainability of secreting VEGF during five days of cell culture (FIG. 3e).

Example 4

Implantation of Microvascular Stamps

Chorioallontoic Membrane (CAM)-Based Angiogenesis Assay.

The function of microvascular stamp to engineering neovessels pattern was examined by implanting the cell-hydrogel construct onto chicken chorioallontoic membrane (CAM) according to a previously developed method[28] (FIG. 15). Fertilized chicken eggs (Hy-Line W-36) were obtained from the University of Illinois Poultry Farm (Urbana, Ill.). The eggs were initially incubated for 7 days, while being placed horizontally inside an incubator at 37° C. and 65% humidity. After the initial incubation period, a small window (1.0×1.0 cm) was created on top of each egg shell by carefully removing shell fragments. After one day of additional incubation to stabilize CAM and the embryos, a gel disk (5-mm diameter, 200-μm thickness) containing fibroblasts with $5 \times 10^6$ cells/ml implanted on top of the CAM of individual embryos. At Days 0, 2, 4 and 7 after implantation, CAM Images were captured using a S6E stereomicroscope (Leica) linked with D-Lux E Camera (Leica). After incubation for seven days, the membrane was fixed with 10% neutral buffered formalin (NBF) for 20 hours. The fixed membrane surrounding the gel structure (10 mm×10 mm) was cut out to image the vascular structure using scanning electron microscopy (SEM, JEOL 7000F SEM). The fixed CAM was washed in PBS several times and subsequently washed in distilled water. Then, the CAM was sequentially dehydrated with 70%, 90% and absolute ethanol and finally dried in air for 24 hours. Finally, all samples were mounted on aluminum stubs, coated with gold particles in a sputter coater, and the surface morphology was examined with SEM.

Finally, fibroblast-encapsulated hydrogels were implanted onto chorioallantoic membrane (CAM) to validate whether the bulk permeability and microchannel geometry of the hydrogels affected the creation of neovessels formation. Implantation of the microchannel-free PEGDA hydrogel onto the CAM (FIG. 4a) stimulated inflammation within two days, most likely because of extravasation of the debris from the dead cells[20] (FIG. 4b-1 & FIG. 16a). This result was similar to inflammation stimulated by a fractured hydrogel that physically exposed the encapsulated cells to host tissue (FIG. 17). In contrast, the microchannel-free PEGDA-MA hydrogel minimally stimulated host inflammation, most likely because of its ability to increase the viability of encapsulated cells (FIG. 16b). However, no specific pattern of neovessels was found with the microchannel-free hydrogels (FIGS. 4b-1 & 4b-2). Remarkably, implantation of the PEGDA-MA hydrogel containing microchannels with diameter of 500 μm stimulated the growth of neovessels along its circular pattern. The spacing between the circular neovessels was the same as that between the microchannels introduced into hydrogel (FIG. 4b-3). Such patterning of neovessels was not achieved with the same hydrogel loaded only with VEGF, rather than the fibroblasts (FIG. 22b).

The diameter of the microchannels in the PEGDA-MA hydrogel was further increased to 1,000 μm to validate the important role of the microchannel geometry on engineering the patterning of neovessels. Interestingly, none of neovessels replicated the circular pattern of microchannels (FIG. 5b & FIG. 12). Most of the neovessels were formed along random paths, as confirmed with bright field image (FIG. 5c). Scanning electron microscope images showed the less compact vascular layer together with red blood cells that likely leaked from the vessels (FIG. 5d).

Taken together, these results demonstrate that the microvascular stamp comprising live cells expressing multiple proangiogenic factors and an engineered hydrogel with proper rigidity, bulk permeability, and microchannel geometry created mature and functional neovessels with desired patterns in live tissue. Specifically, incorporation of hydrophilic methacrylic alginate significantly increased the elastic modulus of the hydrogel by forming elastic intermolecular networks along with PEGDA. The methacrylic alginate further facilitated diffusion-controlled mass flux within the gel, which was imaged with MRI and evaluated using the Fick's law of diffusion. The enhanced mass transport greatly increased the number of viable cells as compared with cells encapsulated in the softer and less permeable hydrogel. In addition, the larger number of cross-links in the PEGDA-MA hydrogel provided cells with a sustainable 3D microenvironment crucial for the elevated expression of proangiogenic factors as compared with cells adhered to the 2D substrate.

In addition, the microchannel geometry guided by the Fick's law of diffusion was another key factor in engineering patterned neovessels. We demonstrated that the surface area of the microchannel introduced into the cell-encapsulated gel mediated the balance between the mass flux through the region of microchannel wall and that through the lower surface of the hydrogel. The proangiogenic factors released through the microchannel wall were possibly localized in the periphery of microchannels. Subsequently, the MMPs secreted by cells likely eroded the tissue surface following the circular pattern of microchannels and multiple proangiogenic factors including VEGF, MCP-1, and proliferin stimulated the growth of mature and functional neovessels through the engraved routes[21-22]. Besides, limited patterning of the neovessels only with VEGF delivery implicates the necessity of using multiple proangiogenic factors to generate mature and functional neovessels with the desired pattern. However, the delivery of multiple growth factors often results in difficulties in regulating their release profiles. Therefore, live cells may be the better source to pattern the neovessels, because of their intrinsic properties of synthesizing and secreting multiple proangiogenic factors in a sustained manner.

Bulk properties of the microvascular stamp played a critical role in activating cellular expression of proangiogenic factors and the geometry of the microchannel patterns regulated the local distribution of proangiogenic factors on the implant site. These two material variables were orchestrated to spatially organize neovessels into the predefined pattern of the microvascular stamp. The stamp can be readily modified with other cell types such as mesenchymal stem cells which also endogenously express multiple proangiogenic growth factors, so the living stamp can be used in various clinical settings[23]. Controlling the 'bottoms-up' emerging behavior of the neovessel formation via 'directed top-down' cues using the living microvascular stamp can be a major step forward in tissue engineering. Therefore, the microvascular stamps of the invention are a powerful tool enabling the improved understanding of vascularization processes in complex tissue development, regeneration and pathogenesis in subjects. Microvascular stamps can be used to improve the control of collateral blood flow in clinical treatments of various diseases and tissue defects. In addition, the design principles established to assemble the microvascular stamp will be useful in designing a broad array of bioimplants and tissue engineering scaffolds to create 'on demand' microvascular networks in an organized fashion.

Example 4

Human bone marrow-derived mesenchymal stem cells (hMSCs) were encapsulated in a stamp of the invention. Vascularization activity of the stamp was observed. Viability of the hMSCs encapsulated in the microvascular stamp was evaluated using a calorimetric assay that measures metabolic activity. A population of hMSCs survived the stereolithographic process and remained viable within the microvascular stamp for at least 7 days. See FIG. 23a. The cellular VEGF secretion level was determined using a human VEGF ELISA kit. The amount of cell-secreted VEGF (■) for five days was 10 times larger than NIH/3T3 cells (●) in the stamp. See FIG. 23b. The microvascular stamps were implanted on CAM membranes and blood vessels were generated with the same pattern as the microchannels. See FIGS. 23c and d.

Therefore, human bone marrow-derived mesenchymal stem cells (hMSCs) were encapsulated into a stamp of the invention and were demonstrated as a stable cell source, along with sustained and high expression of pro-angiogenic growth factors (FIG. 23 a-b). The result is the generation of the growth of new blood vessels within circular patterns of defined spacing (FIG. 23 c).

REFERENCES

1. Dorfleutner et al., Regulation of angiogenesis by tissue factor cytoplasmic domain signaling. *Nature Medicine* 10, 502-509 (2004)
2. Carmeliet, P. & Jain, R. K. Angiogenesis in cancer and other diseases. *Nature* 407, 249-257 (2000)
3. Dor et al., Making vascular networks in the adult: branching morphogenesis without a roadmap. *Trends Cell Bio.* 13, 131-136 (2003)
4. Konerding et al., Evidence for characteristic vascular patterns in solid tumours: quantitative studies using corrosion casts. *Br. J. Cancer* 80, 724-732 (1999)
5. Childs et al., Patterning of angiogenesis in the zebrafish embryo. *Development* 129, 973-982 (2002)
6. Laitakari et al., Size, shape, structure and direction of angiogenesis in laryngeal tumour development. *J. Clin Pathol.* 57, 394-401 (2004)
7. Chen et al., Spatio-temporal VEGF and PDGF delivery patterns blood vessel formation and maturation. *Pharm. Res.* 24, 258-264 (2007)
8. Silva, E. A. & Mooney, D. J. Effects of VEGF temporal and spatial presentation on angiogenesis. *Biomaterials* 31, 1235-1241 (2010)
9. Khademhosseini et al., Microscale technologies for tissue engineering and biology. *Proc. Natl. Acad. Sci.* 103, 2480-2487 (2005)
10. Dike et al., Geometric control of switching between growth, apoptosis, and differentiation during angiogenesis using micropatterned substrates. *In Vitro Cell. Dev. Biol.* 35, 441-448 (1999)
11. Tsuda et al., Cellular control of tissue architectures using a three-dimensional tissue fabrication technique. *Biomaterials* 28, 4939-4946 (2007)
12. Campbell et al., Engineered spatial patterns of FGF-2 immobilized on fibrin direct cell organization. *Biomaterials* 26, 6762-6770 (2005)
13. Gbureck et al., Direct printing of bioceramic implants with spatially localized angiogenic factors. *Adv. Mater.* 19, 795-800 (2007)
14. Du et al., Rapid generation of spatially and temporally controllable long range concentration gradients in a microfluidic device. *Lab on Chip* 9, 761-767 (2009)
15. Barkefors et al., A fluidic device to study directional angiogenesis in complex tissue and organ culture models. *Lab on Chip* 9, 529-536 (2009)
16. Cha et al., Decoupled control of stiffness and permeability of cell-encapsulated poly(ethylene glycol) hydrogel. *Biomaterials* 31, 4864-4871 (2010)
17. Grugel et al., Both v-Ha-Ras and v-Raf stimulate expression of the vascular endothelial growth factor in NIH 3T3 cells. *J. Biol. Chem.* 270, 25915-25919 (1995)
18. Arcaute et al., Stereolithography of three-dimensional bioactive poly(ethylene glycol) constructs with encapsulated cells. *Ann Biomed Eng* 34, 1429-1441 (2006)

19. Chan et al., Three-dimensional photopatterning of hydrogels using stereolithography for long-term cell encapsulation. *Lab on Chip* 10, 2062-2070 (2010)
20. Rock, K. L. & Kono, H. The inflammatory response to cell death. *Annu. Rev. Pathol. Mech. Dis.* 3, 99-126 (2008)
21. Nagase, H. & Woessner, J. F. Matrix metalloproteinases. *J. Biol. Chem.* 274, 21491-21494 (1999)
22. Conway et al., Molecular mechanisms of blood vessel growth. *Cardiovasc. Res.* 49, 507-521 (2001)
23. Kaushal et al., Functional small-diameter neovessels created using endothelial progenitor cells expanded ex vivo. *Nature Medicine* 7, 1035-1040 (2001)
24. Slaughter et al., Hydrogel in regenerative medicine. *Adv. Mater.* 21, 3307-3329 (2009)
25. Choi et al., Microfluidic scaffolds for tissue engineering. *Nature materials* 6, 908-915 (2007)
26. Quijada et al., Swelling monitorization of poly[(N-isopropylacrylamide)-co-(methacrylic acid)] copolymers by magnetic resonance imaging. *Macromolecules* 38, 7434-7442 (2005)
27. Franson, N. M. & Peppas, N. A. Influence of copolymer composition on non-Fickian water transport through glassy copolymers. *J. Appl. Polym. Sci.* 28, 1299-1310 (1983)
28. Staton et al., *Angiogenesis Assays: A critical appraisal of current techniques*, Wiley, New York (2007), chapter 11.

We claim:

1. A method of inducing growth of new blood vessels in a tissue comprising contacting one or more microvascular stamps comprising one or more types of cells encapsulated in a poly(ethylene glycol) (PEGDA) and methacrylic polymer cross-linked hydrogel with the tissue, wherein the cross-linked hydrogel comprises microchannels, wherein the new blood vessels are localized within the lumina of the microchannels, and wherein the one or more microvascular stamps induce growth of new blood vessels in the tissue.

2. The method of claim 1, wherein the one or more types of cells express one or more fusion proteins comprising a growth factor, proangiogenic factor, or antiangiogenic factor fused to a protein light switch.

3. The method of claim 2, wherein the one or more microvascular stamps are illuminated with light at a wavelength of about 450 nm to about 500 nm.

4. The method of claim 1, wherein microscale spacing between the new blood vessels is regulated by microchannel diameter and spacing.

5. The method of claim 1, wherein the microscale spacing between the new blood vessels is about 100 μm to about 2.5 mm on-center.

6. The method of claim 1, wherein the one or more types of cells secrete one or more proangiogenic factors, growth factors, or antiangiogenic factors.

7. The method of claim 1, wherein the microchannels are about 100 μm to about 2.5 mm in diameter and wherein the on-center spacing between the microchannels is about 100 μm to about 2.5 mm.

8. The method of claim 1, wherein the ratio between the flux of growth factors through a microchannel wall of the one or more microvascular stamps ($J_m$) is larger than the flux through a bottom of the one or more microvascular stamps with the same cross-sectional area as the microchannel ($J_r$).

9. The method of claim 1, wherein the one or more microvascular stamps are about 100 μm to about 5 mm thick.

10. The method of claim 1, wherein the one or more microvascular stamps have an elastic modulus of about 10 kPa to about 140 kPa.

11. The method of claim 1, wherein the tissue is in vivo.

12. The method of claim 11, wherein the tissue has a defect and the one or more microvascular stamps are contacted with the defect.

* * * * *

UNITED STATES PATENT AND TRADEMARK OFFICE
CERTIFICATE OF CORRECTION

PATENT NO. : 9,533,073 B1
APPLICATION NO. : 14/709726
DATED : January 3, 2017
INVENTOR(S) : Kong et al.

It is certified that error appears in the above-identified patent and that said Letters Patent is hereby corrected as shown below:

In the Specification

Column 1 Line 3-4:
In Government Interests, delete "This work was supported by US Army Telemedicine & Advanced Technology Research Center (TATRC) (W81XWH-08-1-0701), and National Science Foundation (CAREER: DMR-0847253, STC-EBICS Grant CBET-0939511, IGERT DGE-0965918). The United States govermnent has certain rights in this invention." insert -- This invention was made with governmental support under grant number W81XWH-08-1-0701 awarded by the U.S. Army and grant numbers CAREER: DMR-0847253, STC-EBICS Grant CBET-0939511, IGERT DGE-0965918 awarded by the National Science Foundation. The government has certain rights in this invention. --

Signed and Sealed this
First Day of May, 2018

Andrei Iancu
*Director of the United States Patent and Trademark Office*